US008088828B2

(12) United States Patent
Dalton et al.

(10) Patent No.: US 8,088,828 B2
(45) Date of Patent: Jan. 3, 2012

(54) TREATING BENIGN PROSTATE HYPERPLASIA WITH SARMS

(75) Inventors: James T. Dalton, Lakeland, TN (US); Duane D. Miller, Germantown, TN (US); Mitchell S. Steiner, Germantown, TN (US); Karen A. Veverka, Cordova, TN (US); Wenqing Gao, E.Amherst, NY (US)

(73) Assignee: University of Tennessee Research Foundation, Knoxville, TN (US)

( * ) Notice: Subject to any disclaimer, the term of this patent is extended or adjusted under 35 U.S.C. 154(b) by 0 days.

(21) Appl. No.: 12/826,842

(22) Filed: Jun. 30, 2010

(65) Prior Publication Data
US 2010/0280107 A1 Nov. 4, 2010

Related U.S. Application Data

(63) Continuation of application No. 10/359,270, filed on Feb. 6, 2003, now Pat. No. 7,776,921.

(60) Provisional application No. 60/354,300, filed on Feb. 7, 2002, provisional application No. 60/362,997, filed on Mar. 11, 2002.

(51) Int. Cl.
 *A61K 31/16* (2006.01)
(52) U.S. Cl. ............... 514/616; 514/493; 514/619
(58) Field of Classification Search .......... 514/493, 514/616, 619
See application file for complete search history.

(56) References Cited

U.S. PATENT DOCUMENTS

| | | | |
|---|---|---|---|
| 3,875,229 | A | 4/1975 | Gold |
| 4,139,638 | A | 2/1979 | Neri et al. |
| 4,191,775 | A | 3/1980 | Glen |
| 4,239,776 | A | 12/1980 | Glen et al. |
| 4,282,218 | A | 8/1981 | Glen et al. |
| 4,386,080 | A | 5/1983 | Crossley et al. |
| 4,465,507 | A | 8/1984 | Konno et al. |
| 4,636,505 | A | 1/1987 | Tucker |
| 4,880,839 | A | 11/1989 | Tucker |
| 5,162,504 | A | 11/1992 | Horoszewicz |
| 5,609,849 | A | 3/1997 | Kung |
| 5,656,651 | A | 8/1997 | Sovak et al. |
| 6,019,957 | A | 2/2000 | Miller et al. |
| 6,071,957 | A | 6/2000 | Miller et al. |
| 6,160,011 | A | 12/2000 | Miller et al. |
| 6,242,449 | B1 | 6/2001 | Sato et al. |
| 6,482,861 | B2 | 11/2002 | Miller et al. |
| 6,492,554 | B2 * | 12/2002 | Dalton et al. ............ 564/158 |
| 6,569,896 | B2 * | 5/2003 | Dalton et al. ............ 514/493 |
| 6,838,484 | B2 | 1/2005 | Steiner et al. |
| 6,995,284 | B2 | 2/2006 | Dalton et al. |
| 6,998,500 | B2 | 2/2006 | Dalton et al. |
| 7,041,844 | B2 | 5/2006 | Miller et al. |
| 7,205,437 | B2 * | 4/2007 | Dalton et al. ............ 564/158 |
| 7,547,728 | B2 | 6/2009 | Steiner et al. |
| 2001/0012839 | A1 | 8/2001 | Miller et al. |
| 2003/0232792 | A1 | 12/2003 | Dalton et al. |
| 2007/0161608 | A1 * | 7/2007 | Dalton et al. ............ 514/114 |
| 2009/0264534 | A1 * | 10/2009 | Dalton et al. ............ 514/619 |

FOREIGN PATENT DOCUMENTS

| | | |
|---|---|---|
| EP | 0 040 932 | 2/1981 |
| EP | 0 100 172 | 2/1984 |
| EP | 0 002 892 | 2/1985 |
| EP | 0 253 503 | 12/1991 |
| GB | 1360001 | 3/1970 |
| JP | 52-128329 | 10/1977 |
| JP | 54-63047 | 12/1980 |
| WO | WO 95/19770 | 7/1995 |
| WO | WO 98/05962 | 2/1998 |
| WO | WO 98/53826 | 12/1998 |
| WO | WO 98/55153 | 12/1998 |
| WO | WO 01/27622 | 4/2001 |
| WO | WO 01/28990 | 4/2001 |
| WO | WO 01/34563 | 5/2001 |
| WO | WO 02/00617 | 1/2002 |
| WO | WO 02/16310 | 2/2002 |

OTHER PUBLICATIONS

Byrn et al. Solid-State Chemistry of Drugs, 2d, Chapter 11 Hydrates and Solvates, 233-247.*
Morissette et al. Adv. Drug Delivery Rev. 2004, 56, 275-300.*
I A.M. Rouhi, Chem. & Eng. News, Feb. 24, 2003, 81(8), 32-35.*
U.S. Appl. No. 60/367,355, filed Aug. 24, 2000, Dalton et al.
U.S. Appl. No. 09/644,970, filed Aug. 24, 2000, Dalton et al.
Howard Tucker and Glynne J. Chesterson, J. Med Chem. 1988, 31, pp. 885-887, "Resolution of the Nonsteroidal Antiandrogen—4'-Cyano-3-[(4-fluorophenyl)sulfonyl]-2-hydroxy-2-methyl-3'-(trifluoromethyl)-propionanilide and the Determination of the Absolute Configuration of the Active Enantiomer".

(Continued)

Primary Examiner — Shailendra Kumar
(74) Attorney, Agent, or Firm — Mark S. Cohen; Pearl Cohen Zedek Latzer, LLP

(57) ABSTRACT

This invention provides a method of treating, preventing, suppressing, inhibiting or reducing the incidence of benign prostate hyperplasia in a male subject, by administering to the subject a selective androgen receptor modulator (SARM) and/or its analog, derivative, isomer, metabolite, pharmaceutically acceptable salt, pharmaceutical product, hydrate, N-oxide, or any combination thereof as described herein. This invention also provides a method of treating a subject suffering from hair loss, comprising the step of administering to the subject a therapeutically effective amount of a 5-α reductase enzyme type 1 and/or type 2 inhibitor, wherein said inhibitor is a selective androgen receptor modulator (SARM) and/or its analog, derivative, isomer, metabolite, pharmaceutically acceptable salt, pharmaceutical product, hydrate, N-oxide, or any combination thereof as described herein. This invention also provides a method of inhibiting a 5-α reductase type 1 and/or type 2 enzyme, comprising contacting the enzyme with an effective 5-α reductase inhibitory amount of a selective androgen receptor modulator (SARM) and/or its analog, derivative, isomer, metabolite, pharmaceutically acceptable salt, pharmaceutical product, hydrate, N-oxide, or any combination thereof, as described herein.

15 Claims, 10 Drawing Sheets

OTHER PUBLICATIONS

D. McKillop, et al., "Enantioselective metabolism and pharmacokinetics of Casodex in the male rat", Xenobiotica, 1995, vol. 25, No. 6, 623-634.

Leonid Kirkovsky, et al., "[125I]-Radionated Bicalutamide Analogs as Potential Imaging Agents for Prostate Cancer", Poster Presentation MEDI 155, 214th ACS National Meeting, Las Vegas, NV, Sep. 7-11, 1997, Department of Pharmaceutical Sciences, University of Tennessee, Memphis, TN 38163.

David T. Baird and Anna F. Glasier, "Hormonal Contraception—Drug Therapy", The New England Journal of Medicine, May 27, 1993, pp. 1543-1549.

F.C. W. Wu, "Male Contraception: Current Status and Future Prospects", Clinical Endocrinology, (1988), 29, pp. 443-465.

Carl Djerassi and S.P. Leibo, "A new look at male contraception", Nature, vol. 370, pp. 11-12.

World Health Organisation Task Force on Methods for the Regulation of Male Fertility, "Contraceptive efficacy of testosterone-induced azoospermia in normal men", The Lancet, vol. 336, Oct. 20, 1990, pp. 955-959 and 1517-1518.

C. G. Francisco, et al., "Long-acting contraceptive agents: testosterone esters of unsaturated acids", Steroids, Jan. 1990, vol. 55, Butterworths.

John M. Hoberman and Charles E. Yesalis, "The History of Synthetic Testosterone", Scientific American, Feb. 1995, pp. 76-81.

Leonid Kirkovsky, et al., "Approaches to Irreversible non-steroidal chiral antiandrogens", Department of Pharmaceutical Sciences, University of Tennessee, 47th Southeast/51st Southwest Joint Regional Meeting of the American Chemical Society, Memphis, TN, Nov. 29-Dec. 1, 1995.

David J. Handelsman, "Bridging the gender gap in contraception: another hurdle cleared" The Medical Journal of Australia, vol. 154, Feb. 18, 1996, pp. 230-233.

Edwards JP, Higuchi RI, Winn DT, Pooley CLF, Caferro TR, Hamann LG, Zhi L, Marschke KB, Goldman ME, and Jones TK. Nonsteroidal androgen receptor agonists based on 4-(trifluoromethyl)-2H-pyrano[3,2-g]quinolin-2-one. Bioorg. Med. Chem. Lett., 9: 1003, 1999.

Zhi L, Tegley CM, Marschke KB, and Jones TK. Switching androgen receptor antagonists to agonists by modifying C-ring substituents on piperidino[3,2-g]quinolone. Bioorg. Med. Chem. Lett., 9: 1009, 1999.

Higuchi RI, Edwards JP, Caferro TR, Ringgenberg JD, Kong JW, Hamann LG, Arienti KL, Marschke KB, Davis RL, Farmer LJ, and Jones TK. 4-Alkyl- and 3, 4-diaklyl-1, 2, 3, 4-tetrahydro-8-pyridono [5, 6-g]quinolines: potent, nonsteroidal androgen receptor agonists. Bioorg. Med. Chem. Lett., 9:1335, 1999.

Hamann LG, Mani NS, Davis RL, Wang XN, Marschke KB, and Jones TK. Discovery of a potent, orally active nonsteroidal androgen receptor agonist: 4-ethyl-1,2,3,4-tetrahydro-6-(trifluoromethyl)-8-pyridono[5,6-g]-quinoline (LG121071). J. Med. Chem., 42: 210, 1999.

Rosen J, Day A, Jones TK, Jones ET, Nadzan AM, and Stein RB. Intracellular receptors and signal transducers and activators of transcription superfamilies: novel targets for small-molecule drug discovery. J. Med. Chem., 38: 4855, 1995.

Dalton JT, Mukherjee A, Zhu Z, Kirkovsky L, and Miller DD. Discovery of Nonsteroidal Androgens. Biochem. Biophys. Res. Commun., 244(1):1-4, 1998.

Edwards JP, West SJ, Pooley CLF, Marschke KB, Farmer LJ, and Jones TK. New nonsteroidal androgen receptor modulators based on 4-(trifluoromethyl)-2-(1H)-Pyrololidino[3,2-g]quinolone. Bioorg. Med. Chem. Lett., 8: 745, 1998.

Wenqing, et al (2004) :Comparison of Pharmacological Effects of a Novel Selective Androgen Receptor Modulator, the 5α-Reductase Inhibitor Finasteride, and the Antiandrogen Hydroxyflutamide in Intact Rtas: New Approach for Benign Prostate Hyperplasia Endcrinolgy 145; 5420-5428.

Wenqing, et al Pharmacologic Effects of Androxolutamide(GTx 007) on Male Rats of Varying Hormonal Status. The Endocrine Society, 2002.

Wenqing, et al Pharmacological Effects of a Novel Selective Androgen Receptor Modulator (SARM), Flutamide and Finasteride in Intact Male Rats. The Endocrine Society, 2003 Abstract # P3-221.

Tucker, et al Resolution of the Nom-Steroidal Antiandrogen 4'-Cyano-3[(4-fluorophenyl) sulfonyl]-2-hydroxy-2-methyl-3'-(trifluoromethyl)-propananil and the Determination of the Absolute Configuration of the Active Enantomer.

Wu, et al "Pharmacokinetics and Metabolism of a Selective Androgen Receptor Modulator in Rats: Implication of Molecular Properties and Intensive Metabolic Profile to Investigate Ideal Pharmacokinetic Characterisitcs of a Propanamide in Preclinical Study." Drug Metabolism and Disposition, vol. 34, 483-494.

Donghua, et al "Pharmacodynamics of Selective Androgen Receptor Modulators" The Journal of Pharmacology and Experimental Therapeutics vol. 304; 1334-1340.

Eliason et al., "High Throughput Fluorescence Polarization-Based Screening Assays for the Identification of Novel Nuclear Receptor Ligands," Abstracts of papers, 223rd ACS National Meeting, Orlando, FL, United States, Apr. 7, 2002.

Berger et al., "Concepts and limitations in the application of radiolabeled antiandrogens, estrogens, or androgens as isotropic scanning agents for the prostate", Invest. Urol, 1975, 1391, 10-16.

* cited by examiner

TREATING BENIGN PROSTATE HYPERPLASIA WITH SARMS

CROSS REFERENCE TO RELATED APPLICATIONS

This Application is Continuation Application of U.S. patent application Ser. No. 10/359,270, filed Feb. 6, 2003, now U.S. Pat. No. 7,776,921, which claims the benefit of U.S. Provisional Patent Application Ser. No. 60/354,300, filed Feb. 7, 2002 and Provisional Application Ser. No. 60/362,997, filed Mar. 11, 2002, which are hereby incorporated by reference in their entirety.

FIELD OF INVENTION

This invention relates to the prevention and/or treatment of benign prostate hyperplasia (BPH). More particularly, this invention relates to a method of treating, preventing, suppressing, inhibiting, or reducing benign prostate hyperplasia in a male subject suffering from benign prostate hyperplasia, comprising administering to said subject a selective androgen receptor modulator and/or its analog, derivative, isomer, metabolite, pharmaceutically acceptable salt, pharmaceutical product, hydrate, N-oxide, or mixtures thereof.

BACKGROUND OF THE INVENTION

Benign prostate hyperplasia (BPH) is a nonmalignant enlargement of the prostate gland. BPH is the most common non-malignant proliferative abnormality found in any internal organ and the major cause of morbidity in the adult male. The initial development of BPH begins as early as 30 to 40 years of age and the prevalence is approximately 10% for that age group. With advancing age, the prevalence of BPH increases progressively. BPH occurs in over 75% of men over 50 years of age, reaching 88% prevalence by the ninth decade. The general aging of the United States population, as well as increasing life expectancies, is anticipated to contribute to the continued growth in the number of BPH sufferers.

BPH frequently results in a gradual squeezing of the portion of the urethra which traverses the prostate (prostatic urethra). This causes patients to experience a frequent urge to urinate because of incomplete emptying of the bladder and a burning sensation or similar discomfort during urination. The obstruction of urinary flow can also lead to a general lack of control over urination, including difficulty initiating urination when desired, as well as difficulty of urinary retention because bladder outlet obstruction and a uncontrollable urinary continence due to residual urine, a condition known as overflow urinary incontinence.

There are two components of BPH. The first component is due to enlargement of the prostate gland, which may result in compression of the urethra and obstruction to the flow of urine from the bladder. The second component is due to increased smooth muscle tone of the bladder neck and the prostate itself, which interferes with emptying of the bladder and is regulated by α1 adrenergic receptors (α1-Ars).

The androgens testosterone and dihydrotestosterone (DHT) are contributing factors in producing BPH in the prostate. Testosterone is converted by 5-alpha-reductase (5α-reductase) to DHT, which is about five times more potent than testosterone due to its greater binding affinity to the androgen receptor. DHT binds to cytoplasmic receptors in the prostate, where it initiates RNA and DNA synthesis. This action, in turn, induces protein synthesis and abnormal growth of the prostate. There are two isoforms of 5-α reductase in mammals, particularly humans. The type 1 isoenzyme is highly expressed in liver and skin, has a lower affinity for testosterone, and behaves more like a catabolic reagent. In contrast, the type 2 isoenzyme is mainly expressed in androgen target tissues, has higher affinity for testosterone, and amplifies the androgenic effects of testosterone by converting it into DHT.

Androgen deprivation can decrease the obstructive symptoms of BPH. Moreover, current clinical evidence indicates that inhibition of 5α-reductase reverses the symptoms of BPH in human males (Strauch, G. et al., Eur. Urol., Vol. 26, pp. 247-252 (1994); Rhodes, L. et al., Prostate, Vol. 22, pp. 43-51 (1993)). Further, 5α-reductase activity appears to be higher in cells obtained from BPH tissue than from normal prostate tissue. (Bone, K., The European Journal of Herbal Medicine, Vol. 4(1), pp. 15-24 (1998)).

Knowledge of how 5α-reductase regulates prostate growth has resulted in the development of drugs, such as the 5α-reductase type 2 selective inhibitor finasteride, for use in controlling the symptoms of BPH and in preventing urinary retention. Finasteride (PROSCAR) blocks the conversion of testosterone to DHT and has been found to reduce the size of the prostate, leading to an increase in peak urinary flow rate and a reduction in symptoms (Strauch et al. 1994; Rhodes et al. 1993; Russel et al (1994), Annu. Rev. Biochem. 63: 25-61).

Patients diagnosed with BPH generally have several options for treatment, including watchful waiting, surgical intervention, laser assisted prostatectomy, thermal therapies, and drug therapy. Watchful waiting is often chosen by men who are not or minimally bothered by the symptoms of BPH, and it includes regular checkups and monitoring to see if the condition remains tolerable. Surgical intervention is the currently accepted treatment for BPH and is generally reserved for patients with intolerable symptoms or those with significant potential symptoms if treatment is withheld. Currently, of the patients suffering from BPH, only a very small fraction (2-3%) is being treated by surgery. Surgical therapy includes including transurethral resection of the prostate (TURP), transurethral incision of the prostate (TUIP), and open surgery. Surgical procedures, while effective in relieving the symptoms of BPH, result in substantial damage being inflicted upon the prostatic urethra. Laser assisted prostatectomy and heat ablation therapies, while less invasive, also cause substantial damage to the prostatic urethra. As well, surgical treatment of BPH is estimated to cost over a billion dollars per year, with the expectation that these costs will rise as the aged male population increases.

Drugs useful for the treatment of BPH are designed to treat prostate enlargement, which characterizes BPH, by shrinking the prostate or by inhibiting or slowing the growth of prostate cells. Finasteride (Proscar®, Merck) is one such therapy which is indicated for the treatment of symptomatic BPH. Finasteride is a competitive inhibitor of the enzyme 5α-reductase type 2, which is responsible for the conversion of testosterone to dihydrotestosterone in the prostate gland. Other drugs are designed to relax the muscles in the prostate and bladder neck to relieve urethral obstruction. Terazosin (Hytrin, Abbott) is an adrenergic receptor blocking agent (α 1-AR blockers) which acts by decreasing the smooth muscle tone within the prostate gland, urethro and bladder.

BPH, if left unabated, can have dire health consequences. BPH can lead to acute urinary retention (complete inability to urinate), serious life threatening urinary tract infections and urosepsis and permanent bladder and kidney damage. Innovative approaches are urgently needed at both the basic science and clinical levels to treat BPH. The development of new non-invasive therapeutic approaches could result in a substantial increase in the number of BPH patients who elect to receive therapy. The present invention is directed to satisfying this need.

SUMMARY OF THE INVENTION

In one embodiment, this invention relates to a method of treating a male subject suffering from benign prostate hyperplasia, comprising the step of administering to the subject a selective androgen receptor modulator (SARM) and/or its analog, derivative, isomer, metabolite, pharmaceutically acceptable salt, pharmaceutical product, hydrate, N-oxide, or any combination thereof.

In another embodiment, this invention relates to a method of preventing, suppressing, inhibiting or reducing the incidence of benign prostate hyperplasia in a male subject, comprising the step of administering to the subject a selective androgen receptor modulator (SARM) and/or its analog, derivative, isomer, metabolite, pharmaceutically acceptable salt, pharmaceutical product, hydrate, N-oxide, or any combination thereof.

In another embodiment, this invention relates to a method of treating a subject suffering from hair loss, comprising the step of administering to said subject a therapeutically effective amount of a 5-α reductase enzyme inhibitor, wherein said inhibitor is a selective androgen receptor modulator (SARM) and/or its analog, derivative, isomer, metabolite, pharmaceutically acceptable salt, pharmaceutical product, hydrate, N-oxide, or any combination thereof.

This invention further relates to a method of inhibiting a 5-α reductase enzyme, comprising contacting the enzyme with an effective 5-α reductase inhibitory amount of a selective androgen receptor modulator (SARM) and/or its analog, derivative, isomer, metabolite, pharmaceutically acceptable salt, pharmaceutical product, hydrate, N-oxide, or any combination thereof.

In one embodiment, the SARM which: a) treats, prevents, inhibits, or suppresses BPH; and/or b) treats hair loss; and/or c) inhibits 5α-reductase enzyme; and/or d) antagonizes the androgen receptor, is a compound represented by the structure of formula I.

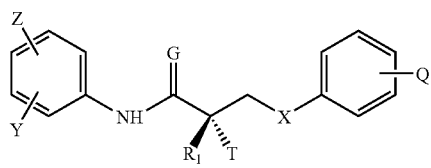

I wherein
G is O or S;
X is a bond, O, $CH_2$, NH, Se, PR, NO or NR;
T is OH, OR, —$NHCOCH_3$, or NHCOR
Z is $NO_2$, CN, COOH, COR, NHCOR or CONHR;
Y is $CF_3$, F, I, Br, Cl, CN, $C(R)_3$ or $Sn(R)_3$;
Q is alkyl, halogen, $CF_3$, CN, $C(R)_3$, $Sn(R)_3$, $N(R)_2$, $NHCOCH_3$, $NHCOCF_3$, NHCOR, NHCONHR, NHCOOR, OCONHR, CONHR, $NHCSCH_3$, $NHCSCF_3$, NHCSR, $NHSO_2CH_3$, $NHSO_2R$, OR, COR, OCOR, $OSO_2R$, $SO_2R$, SR; or Q together with the benzene ring to which it is attached is a fused ring system represented by structure A, B or C:

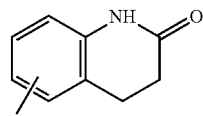

A

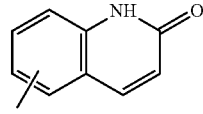

B

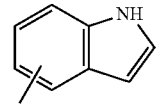

C

R is alkyl, haloalkyl, dihaloalkyl, trihaloalkyl, $CH_2F$, $CHF_2$, $CF_3$, $CF_2CF_3$, aryl, phenyl, halogen, alkenyl or OH; and
$R_1$ is $CH_3$, $CH_2F$, $CHF_2$, $CF_3$, $CH_2CH_3$, or $CF_2CF_3$.

In another embodiment, the SARM which: a) treats, prevents, inhibits, or suppresses BPH; and/or b) treats hair loss; and/or c) inhibits 5α-reductase enzyme; and/or d) antagonizes the androgen receptor is a compound represented by the structure of formula II.

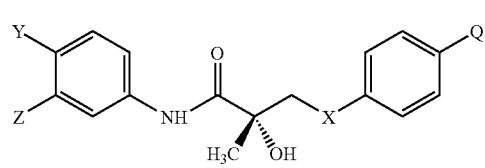

II wherein
X is a bond, O, $CH_2$, NH, Se, PR, NO or NR;
Z is $NO_2$, CN, COOH, COR, NHCOR or CONHR;
Y is $CF_3$, F, I, Br, Cl, CN, $C(R)_3$ or $Sn(R)_3$;
Q is alkyl, halogen, $CF_3$, CN, $C(R)_3$, $Sn(R)_3$, $N(R)_2$, $NHCOCH_3$, $NHCOCF_3$, NHCOR, NHCONHR, NHCOOR, OCONHR, CONHR, $NHCSCH_3$, $NHCSCF_3$, NHCSR, $NHSO_2CH_3$, $NHSO_2R$, OR, COR, OCOR, $OSO_2R$, $SO_2R$, SR; or Q together with the benzene ring to which it is attached is a fused ring system represented by structure A, B or C:

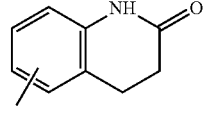

A

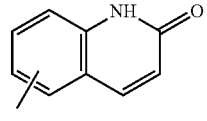

B

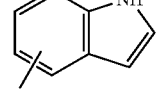

C

R is alkyl, haloalkyl, dihaloalkyl, trihaloalkyl, $CH_2F$, $CHF_2$, $CF_3$, $CF_2CF_3$, aryl, phenyl, halogen, alkenyl or OH.

In another embodiment, the SARM which: a) treats, prevents, inhibits, or suppresses BPH; and/or b) treats hair loss; and/or c) inhibits 5α-reductase enzyme; and/or d) antagonizes the androgen receptor is a compound represented by the structure of formula III.

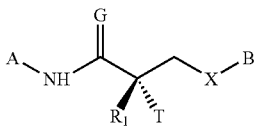

wherein
X is a bond, O, CH$_2$, NH, Se, PR, NO or NR;
G is O or S;
R$_1$ is CH$_3$, CH$_2$F, CHF$_2$, CF$_3$, CH$_2$CH$_3$, or CF$_2$CF$_3$;
T is OH, OR, —NHCOCH$_3$, or NHCOR;
R is alkyl, haloalkyl, dihaloalkyl, trihaloalkyl, CH$_2$F, CHF$_2$, CF$_3$, CF$_2$CF$_3$, aryl, phenyl, halogen, alkenyl or OH;
A is a ring selected from:

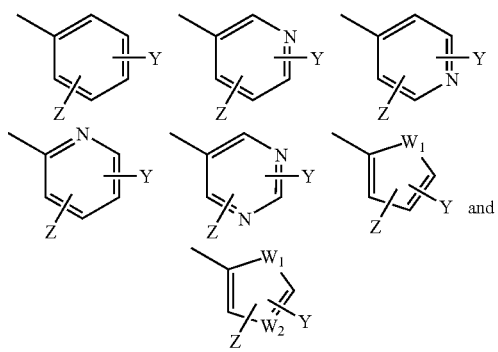

B is a ring selected from:

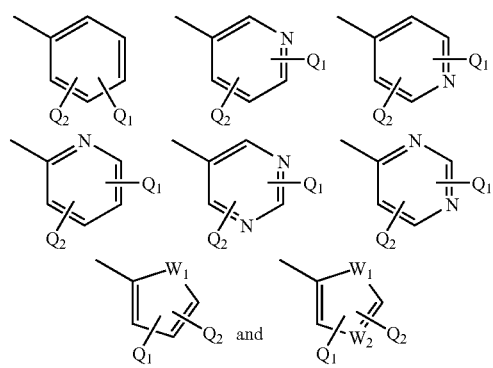

wherein
A and B cannot simultaneously be a benzene ring;
Z is NO$_2$, CN, COOH, COR, NHCOR or CONHR;
Y is CF$_3$, F, I, Br, Cl, CN, C(R)$_3$ or Sn(R)$_3$;
Q$_1$ and Q$_2$ are independently of each other a hydrogen, alkyl, halogen, CF$_3$, CN, C(R)$_3$, Sn(R)$_3$, N(R)$_2$, NHCOCH$_3$, NHCOCF$_3$, NHCOR, NHCONHR, NHCOOR, OCONHR, CONHR, NHCSCH$_3$, NHCSCF$_3$, NHCSR, NHSO$_2$CH$_3$, NHSO$_2$R, OR, COR, OCOR, OSO$_2$R, SO$_2$R, SR,

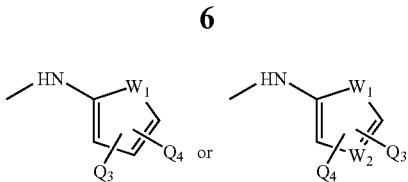

Q$_3$ and Q$_4$ are independently of each other a hydrogen, alkyl, halogen, CF$_3$, CN, C(R)$_3$, Sn(R)$_3$, N(R)$_2$, NHCOCH$_3$, NHCOCF$_3$, NHCOR, NHCONHR, NHCOOR, OCONHR, CONHR, NHCSCH$_3$, NHCSCF$_3$, NHCSR, NHSO$_2$CH$_3$, NHSO$_2$R, OR, COR, OCOR, OSO$_2$R, SO$_2$R or SR;
W$_1$ is O, NH, NR, NO or S; and
W$_2$ is N or NO.

In another embodiment, the SARM which: a) treats, prevents, inhibits, or suppresses BPH; and/or b) treats hair loss; and/or c) inhibits 5α-reductase enzyme; and/or d) antagonizes the androgen receptor is a compound represented by the structure of formula IV.

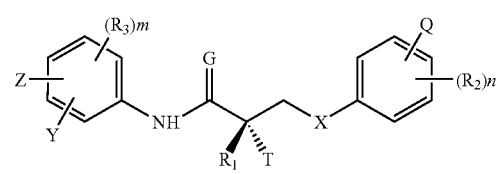

wherein
X is a bond, O, CH$_2$, NH, Se, PR, NO or NR;
G is O or S;
T is OH, OR, —NHCOCH$_3$, or NHCOR;
R is alkyl, haloalkyl, dihaloalkyl, trihaloalkyl, CH$_2$F, CHF$_2$, CF$_3$, CF$_2$CF$_3$, aryl, phenyl, halogen, alkenyl or OH;
R$_1$ is CH$_3$, CH$_2$F, CHF$_2$, CF$_3$, CH$_2$CH$_3$, or CF$_2$CF$_3$;
R$_2$ is F, Cl, Br, I, CH$_3$, CF$_3$, OH, ON, NO$_2$, NHCOCH$_3$, NHCOCF$_3$, NHCOR, alkyl, arylalkyl, OR, NH$_2$, NHR, N(R)$_2$, SR;
R$_3$ is F, Cl, Br, I, ON, NO$_2$, COR, COOH, CONHR, CF$_3$, SnR$_3$, or R$_3$ together with the benzene ring to which it is attached forms a fused ring system represented by the structure:

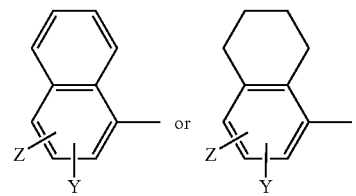

Z is NO$_2$, CN, COR, COOH, or CONHR;
Y is CF$_3$, F, Br, Cl, I, CN, or Sn(R)$_3$;
Q is H, alkyl, halogen, CF$_3$, CN, C(R)$_3$, Sn(R)$_3$, N(R)$_2$, NHCOCH$_3$, NHCOCF$_3$, NHCOR, NHCONHR, NHCOOR, OCONHR, CONHR, NHCSCH$_3$, NHCSCF$_3$, NHCSR, NHSO$_2$CH$_3$, NHSO$_2$R, OH, OR, COR, OCOR, OSO$_2$R, SO$_2$R, SR; or Q together with the benzene ring to which it is attached is a fused ring system represented by structure A, B or C:

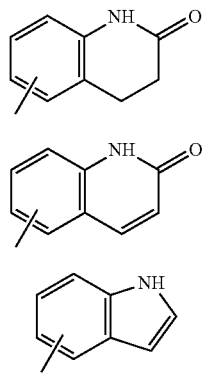

n is an integer of 1-4; and
m is an integer of 1-3.

In another embodiment, the SARM which: a) treats, prevents, inhibits, or suppresses BPH; and/or b) treats hair loss; and/or c) inhibits 5α-reductase enzyme; and/or d) antagonizes the androgen receptor is a compound represented by the structure of formula V.

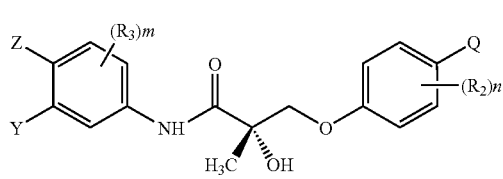

wherein
$R_2$ is F, Cl, Br, I, $CH_3$, $CF_3$, OH, CN, $NO_2$, $NHCOCH_3$, $NHCOCF_3$, NHCOR, alkyl, arylalkyl, OR, $NH_2$, NHR, $N(R)_2$, SR;
$R_3$ is F, Cl, Br, I, CN, $NO_2$, COR, COOH, CONHR, $CF_3$, $SnR_3$, or $R_3$ together with the benzene ring to which it is attached forms a fused ring system represented by the structure:

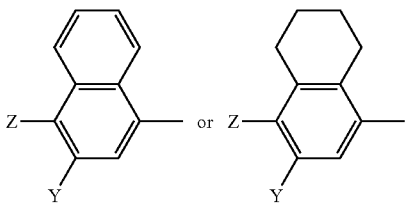

R is alkyl, haloalkyl, dihaloalkyl, trihaloalkyl, $CH_2F$, $CHF_2$, $CF_3$, $CF_2CF_3$, aryl, phenyl, halogen, alkenyl or OH;
Z is $NO_2$, CN, COR, COOH, or CONHR;
Y is $CF_3$, F, Br, Cl, I, CN, or $SnR_3$;
Q is H, alkyl, halogen, $CF_3$, CN, $C(R)_3$, $Sn(R)_3$, $N(R)_2$, $NHCOCH_3$, $NHCOCF_3$, NHCOR, NHCONHR, NHCOOR, OCONHR, CONHR, $NHCSCH_3$, $NHCSCF_3$, NHCSR, $NHSO_2CH_3$, $NHSO_2R$, OH, OR, COR, OCOR, $OSO_2R$, $SO_2R$, SR; or Q together with the benzene ring to which it is attached is a fused ring system represented by structure A, B or C:

n is an integer of 1-4; and
m is an integer of 1-3.

In another embodiment, the SARM which: a) treats, prevents, inhibits, or suppresses BPH; and/or b) treats hair loss; and/or c) inhibits 5α-reductase enzyme; and/or d) antagonizes the androgen receptor is a compound represented by the structure of formula VI.

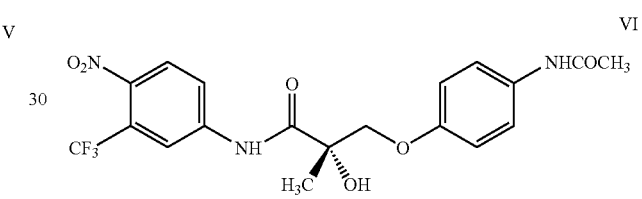

In another embodiment, the SARM which: a) treats, prevents, inhibits, or suppresses BPH; and/or b) treats hair loss; and/or c) inhibits 5α-reductase enzyme; and/or d) antagonizes the androgen receptor is a compound represented by the structure of formula VII.

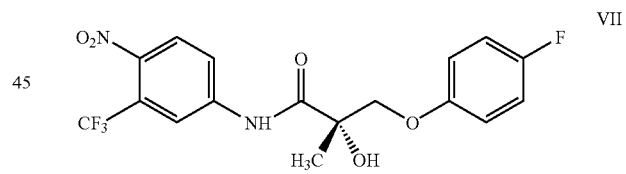

In one embodiment, the SARM which: a) treats, prevents, inhibits, or suppresses BPH; and/or b) treats hair loss; and/or c) inhibits 5α-reductase enzyme; and/or d) antagonizes the androgen receptor is a compound represented by the structure of formula VIII.

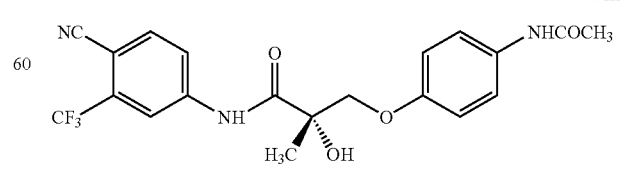

In one embodiment, the SARM which: a) treats, prevents, inhibits, or suppresses BPH; and/or b) treats hair loss; and/or c) inhibits 5α-reductase enzyme; and/or d) antagonizes the androgen receptor is a compound represented by the structure of formula IX.

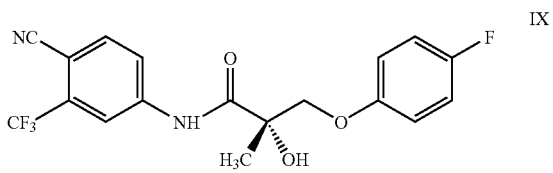

In another embodiment, the SARM is an androgen receptor agonist. In another embodiment, the SARM is an androgen receptor antagonist. In another embodiment, the SARM is an inhibitor of 5α-reductase enzyme. In another embodiment, the SARM is a competitive inhibitor of 5α-reductase enzyme.

In one embodiment, the 5-α reductase enzyme is a type 1 5-α reductase enzyme. In another embodiment, the 5-α reductase enzyme is a type 2 5-α reductase enzyme. In another embodiment, the 5-α reductase enzyme is a testosterone 5-α reductase enzyme, i.e. the enzyme which converts testosterone (T) to dihydrotestosterone (DHT).

This invention provides in one embodiment a method of blocking the ability of DHT to induce hyperplasia comprising contacting the Androgen Receptor with any one or more of Compound I-IX or a composition comprising any one or more of Compound I-IX, thereby blocking the ability of DHT to induce hyperplasia. In one embodiment, the compound is Compound VII. In another embodiment, the compound is Compound VI.

This invention provides in one embodiment a method of blocking the ability of DHT to induce hyperplasia comprising contacting the Androgen Receptor with any one or more of Compound I-IX or a composition comprising any one or more of Compound I-IX, thereby blocking the ability of DHT to induce hyperplasia. In one embodiment, the compound is Compound VII. In another embodiment, the compound is Compound VI.

In one embodiment, Compound I-IX is a partial agonist and selective agonist that upon contact with the Androgen Receptor or by administration in a subject prevents mitogenic action of Testosterone and DHT by blocking the ability of endogenous ligands to bind to the receptor. In one embodiment, the compound is Compound VII. In another embodiment, the compound is Compound VI.

In one embodiment, the Compound I-IX prevents recruitment of co-activators or co-regulators of androgen-responsive DNA and prevents growth of AR-dependent cells (such as glandular epithelium in prostate). In one embodiment, the compound is Compound VII. In another embodiment, the compound is Compound VI.

In one embodiment, the Compound I-IX prevents recruiting co-repressors of androgen-responsive DNA and prevents growth of AR-dependent cells (such as glandular epithelium in prostate). In one embodiment, the compound is Compound VII. In another embodiment, the compound is Compound VI.

In one embodiment, the Compound I-IX prevents mitogenic action of Testosterone and DHT by blocking the ability of endogenous ligands to bind the receptor and induces the transcription of other hormones and growth factors which signal in a paracrine fashion to induce proliferation of prostate epithelium. In one embodiment, the compound is Compound VII. In another embodiment, the compound is Compound VI.

In one embodiment, the Compound I-IX prevents mitogenic action of Testosterone and DHT by blocking the ability of endogenous ligands to bind the receptor and induce downstream molecular signaling which induce programmed cell death of glandular epithelium. In one embodiment, the compound is Compound VII. In another embodiment, the compound is Compound VI.

The present invention provides a safe and effective method of treating, preventing, suppressing, inhibiting or reducing the incidence of BPH and is particularly useful in treating male subjects suffering from symptoms and signs of BPH.

DETAILED DESCRIPTION OF THE INVENTION

Figure 1:
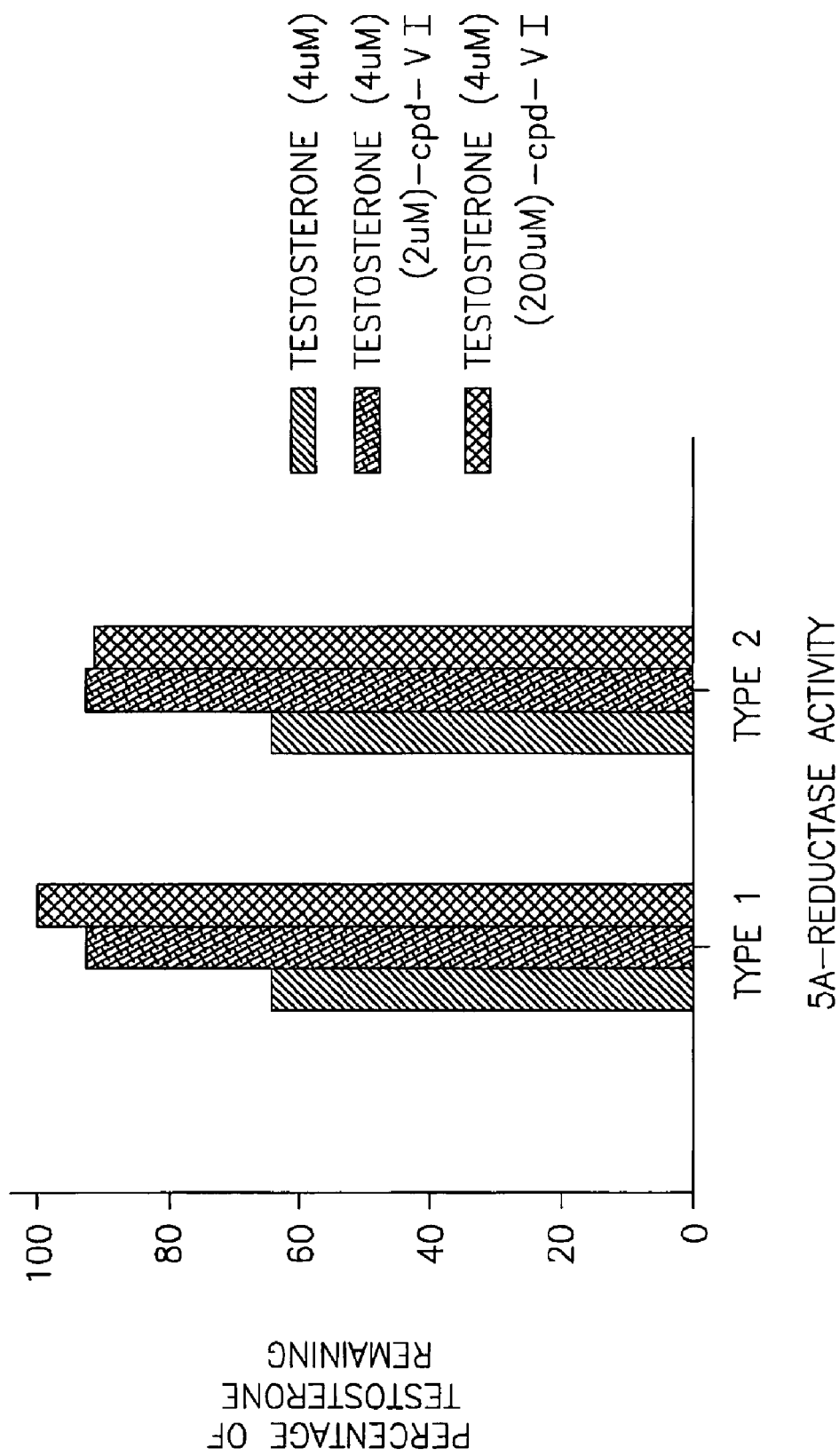
FIG. 1. Effects of Compound VI, a SARM, on the metabolism of testosterone by type 1 and type 2 5•-reductase (n=3). Data were normalized to the UV absorbance readings obtained from a •-galactosidase assay.
Figure 2A:
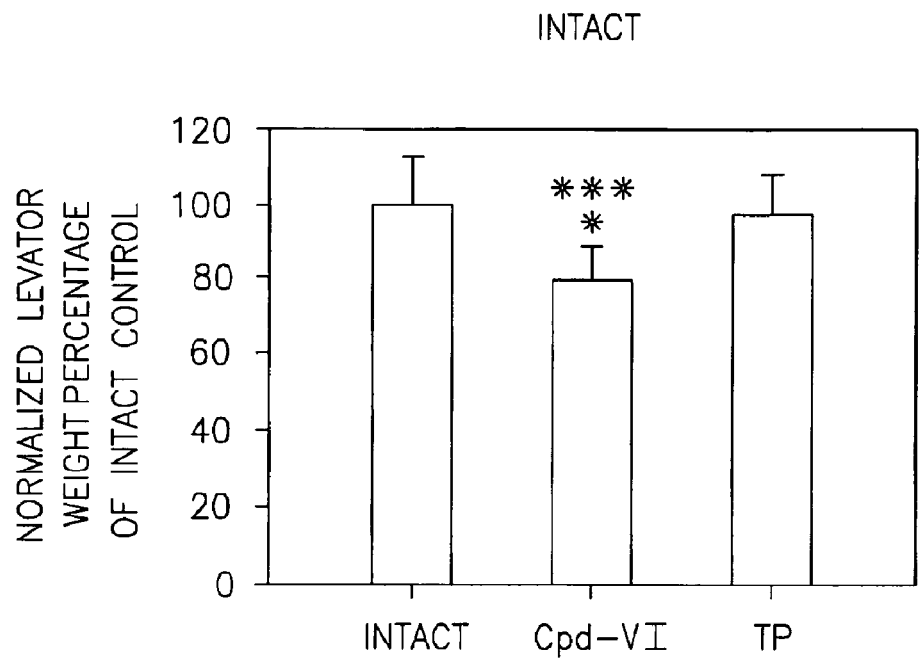
FIG. 2. Effects of Compound VI on the size of prostate of seminal vesicles and levator ani muscle in rats of varying hormonal status.
Figure 2B:
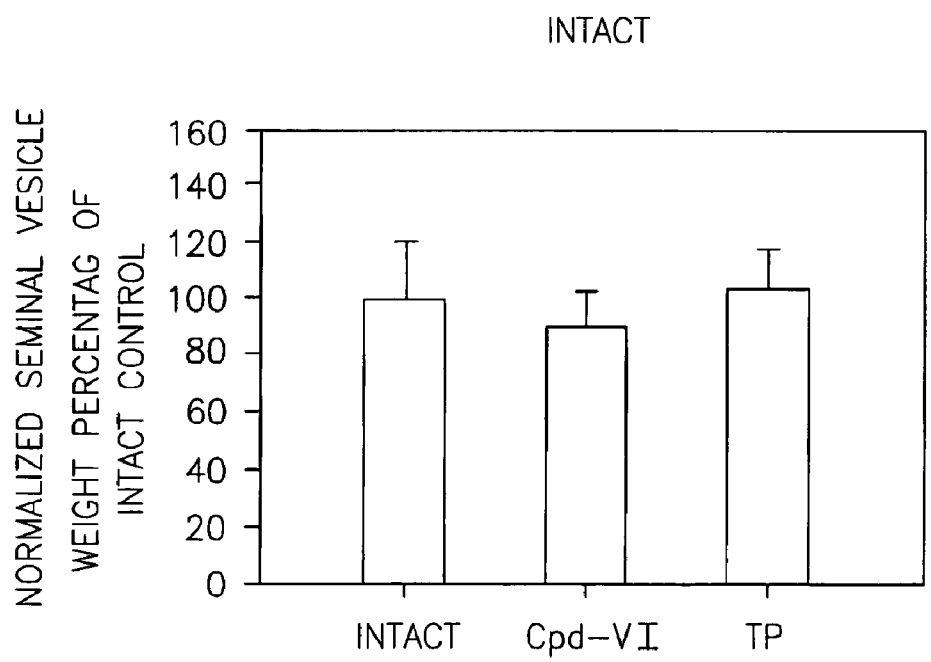
Figure 2C:
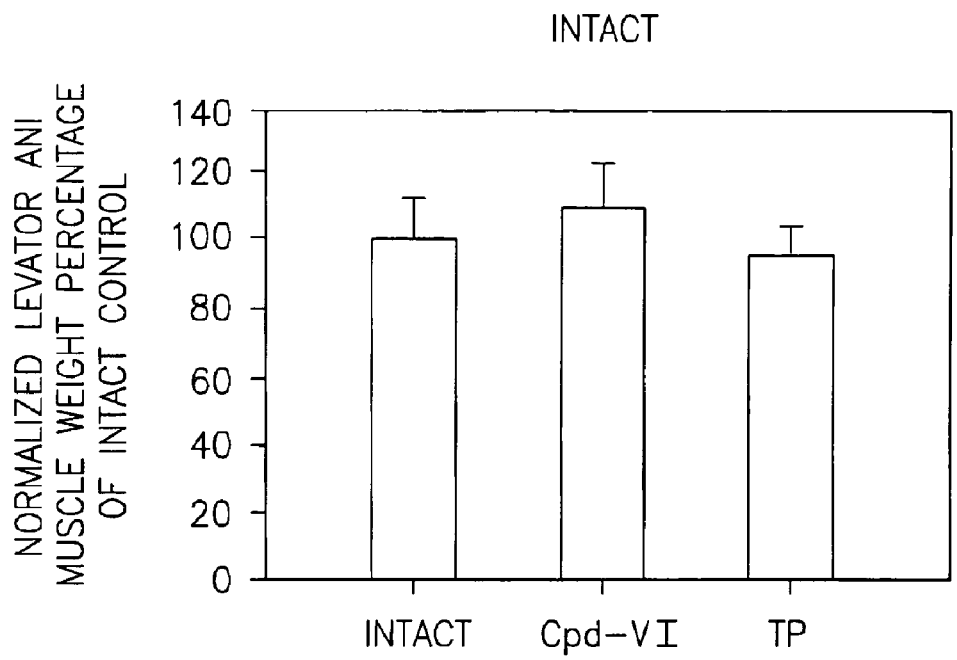
Figure 2D:
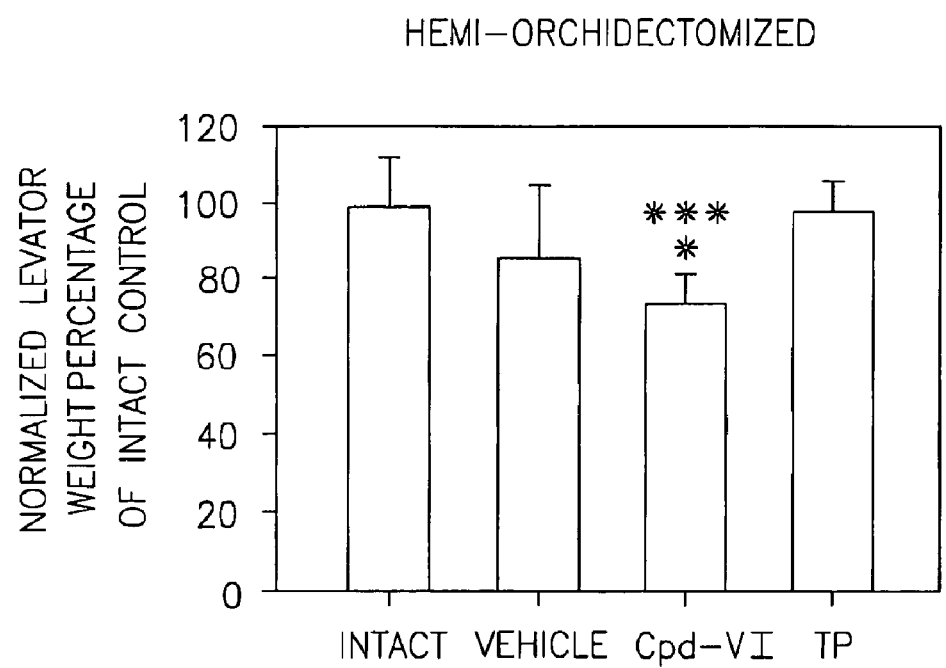
Figure 2E:
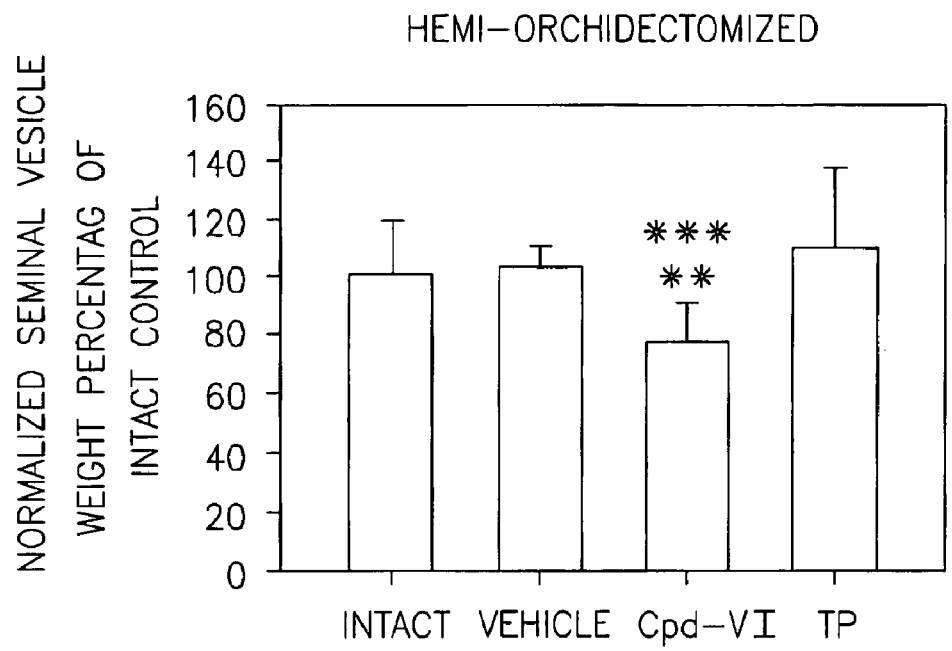
Figure 2F:
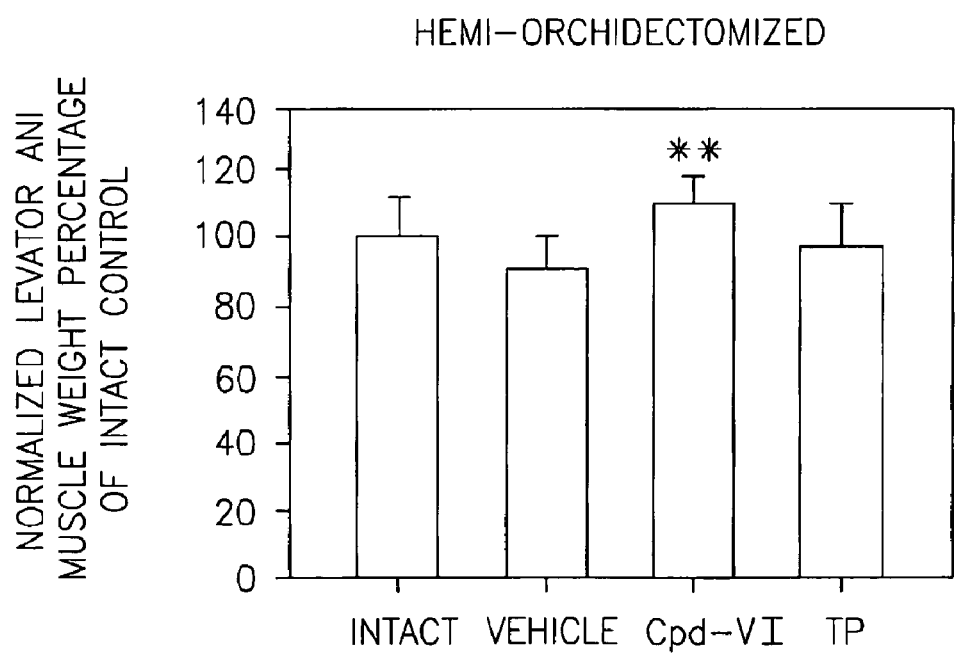
Figure 2G:
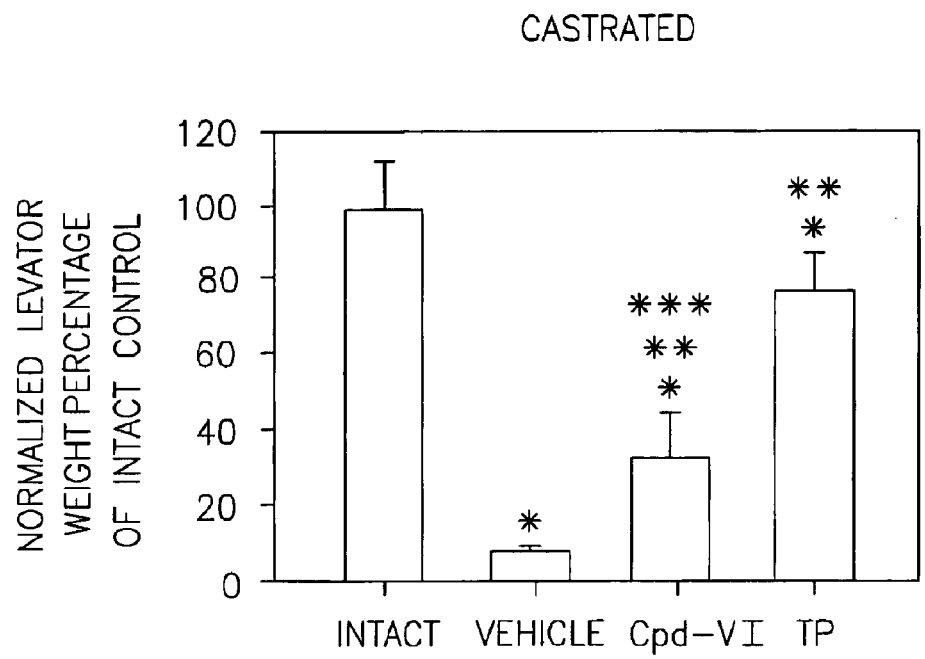
Figure 2H:
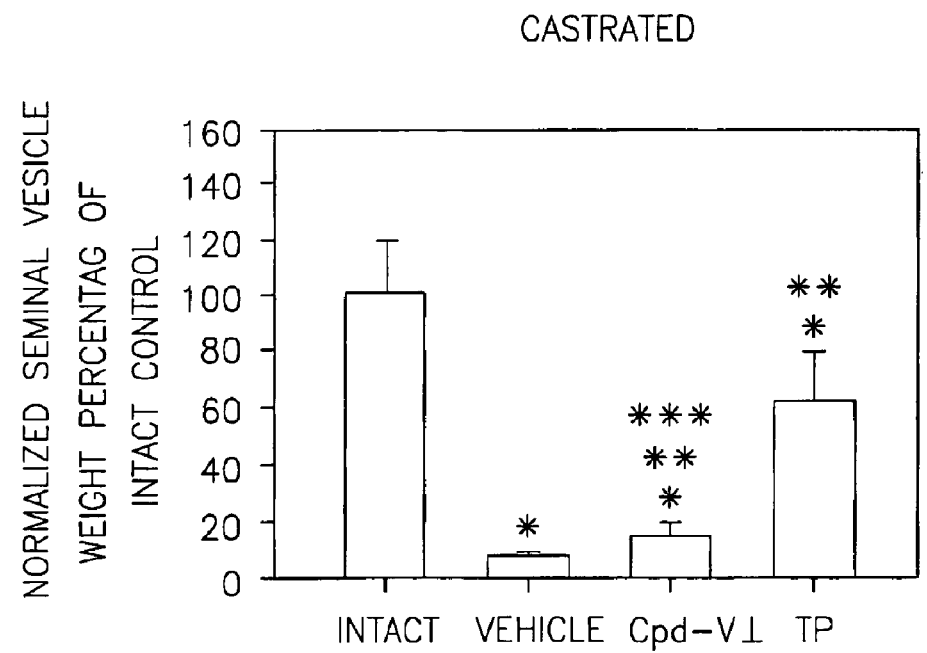
Figure 2I:
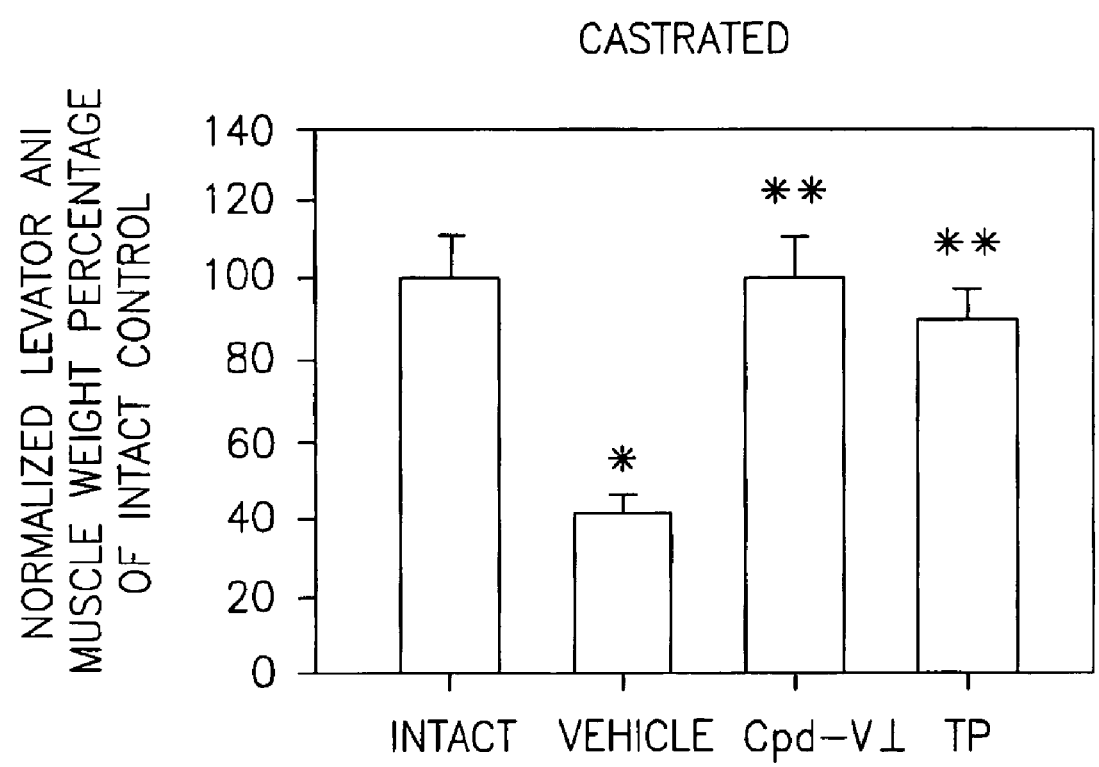

In one embodiment, this invention provides a method of treating, preventing, suppressing, inhibiting or reducing the incidence of benign prostate hyperplasia in a male subject, by administering to the subject a selective androgen receptor modulator (SARM). In another embodiment, the method includes administering an analog of the SARM. In another embodiment, the method includes administering a derivative of the SARM. In another embodiment, the method includes administering an isomer of the SARM. In another embodiment, the method includes administering a metabolite of the SARM. In another embodiment, the method includes administering a pharmaceutically acceptable salt of the SARM. In another embodiment, the method includes administering a hydrate of the SARM. In another embodiment, the method includes administering an N-oxide of the SARM. In another embodiment, the method includes administering a pharmaceutical product of the SARM.

This invention provides in one embodiment a method of blocking the ability of DHT to induce hyperplasia comprising contacting the Androgen Receptor with any one or more of Compound I-IX or a composition comprising any one or more of Compound I-IX, thereby blocking the ability of DHT to induce hyperplasia. In one embodiment, the compound is Compound VII. In another embodiment, the compound is Compound VI.

This invention provides in one embodiment a method of blocking the ability of DHT to induce hyperplasia comprising contacting the Androgen Receptor with any one or more of Compound I-IX or a composition comprising any one or more of Compound I-IX, thereby blocking the ability of DHT to induce hyperplasia. In one embodiment, the compound is Compound VII. In another embodiment, the compound is Compound VI.

In one embodiment, Compound I-IX is a partial agonist and selective agonist that upon contact with the Androgen Receptor or by administration in a subject prevents mitogenic action of Testosterone and DHT by blocking the ability of endogenous ligands to bind to the receptor. In one embodiment, the compound is Compound VII. In another embodiment, the compound is Compound VI.

In one embodiment, the Compound I-IX prevents recruitment of co-activators or co-regulators of androgen-responsive DNA and prevents growth of AR-dependent cells (such as glandular epithelium in prostate). In one embodiment, the compound is Compound VII. In another embodiment, the compound is Compound VI.

In one embodiment, the Compound I-IX prevents recruiting co-repressors of androgen-responsive DNA and prevents growth of AR-dependent cells (such as glandular epithelium in prostate). In one embodiment, the compound is Compound VII. In another embodiment, the compound is Compound VI.

In one embodiment, the Compound I-IX prevents mitogenic action of Testosterone and DHT by blocking the ability of endogenous ligands to bind the receptor and induces the transcription of other hormones and growth factors which signal in a paracrine fashion to induce proliferation of prostate epithelium. In one embodiment, the compound is Compound VII. In another embodiment, the compound is Compound VI.

In one embodiment, the Compound I-IX prevents mitogenic action of Testosterone and DHT by blocking the ability of endogenous ligands to bind the receptor and induce downstream molecular signaling which induce programmed cell death of glandular epithelium. In one embodiment, the compound is Compound VII. In another embodiment, the compound is Compound VI.

In one embodiment, Compounds I-IX is a selective agonist in muscle and a partial agonist in prostate. Androgen action is mediated through the Androgen Receptor (AR). AR is a ligand-dependent transcription factor that controls the expression of androgen-response genes by binding to androgen-response elements in DNA. Androgen-responsive genes are responsible for androgen-dependent proliferation and also androgen-dependent cell death. Also, other genes in cellular signaling cascades contribute to cellular proliferation or repression by signaling through the AR and in sequence with AR (upregulated by interaction with AR-dependent DNA, however, are mitogenic through alternative receptor involved in cellular proliferation (i.e. IGF-I). Prostate is an androgen-sensitive tissue; thus Testosterone and DHT maintain normal structural and functional integrity of prostate (via AR). However, T and DHT are also potent mitogens in prostate and can lead to abnormal growth of AR-dependent cells (such as prostatic glandular epithelial cells) with the ultimate consequence being prostatic disease like BPH and cancer. Depletion of the androgenic support by castration or inhibition of endogenous ligands for AR (such as partial agonists such as Compound I-IX) prevents the metabolic changes dependent on Testosterone and DHT.

In another embodiment, this invention also provides a method of treating a subject suffering from hair loss, comprising the step of administering to the subject a therapeutically effective amount of a 5-α reductase type 1 and/or type 2 enzyme inhibitor, wherein the inhibitor is a selective androgen receptor modulator (SARM). In another embodiment, the method includes administering an analog of the SARM. In another embodiment, the method includes administering a derivative of the SARM. In another embodiment, the method includes administering an isomer of the SARM. In another embodiment, the method includes administering a metabolite of the SARM. In another embodiment, the method includes administering a pharmaceutically acceptable salt of the SARM. In another embodiment, the method includes administering a hydrate of the SARM. In another embodiment, the method includes administering an N-oxide of the SARM.

In another embodiment, this invention also provides a method of inhibiting a 5-α reductase type 1 and/or type 2 enzyme, comprising contacting the enzyme with an effective 5-α reductase inhibitory amount of a selective androgen receptor modulator (SARM). In another embodiment, the method includes administering an analog of the SARM. In another embodiment, the method includes administering a derivative of the SARM. In another embodiment, the method includes administering an isomer of the SARM. In another embodiment, the method includes administering a metabolite of the SARM. In another embodiment, the method includes administering a pharmaceutically acceptable salt of the SARM. In another embodiment, the method includes administering a hydrate of the SARM. In another embodiment, the method includes administering an N-oxide of the SARM.

Selective androgen receptor modulators (SARMs) are a class of androgen receptor targeting agents (ARTA), which demonstrate androgenic and anabolic activity of a nonsteroidal ligand for the androgen receptor. These novel agents are useful in males and females for the treatment of a variety of hormone-related conditions, such as hypogonadism, sarcopenia, erythropoiesis, erectile dysfunction, lack of libido, osteoporosis and infertility. Further, SARMs are useful for oral testosterone replacement therapy, treating prostate cancer, imaging prostate cancer, and maintaining sexual desire in women.

In one embodiment, the SARM which: a) treats, prevents, inhibits, or suppresses BPH; and/or b) treats hair loss; and/or c) inhibits 5α-reductase enzyme; and/or d) antagonizes the androgen receptor is a compound represented by the structure of formula I.

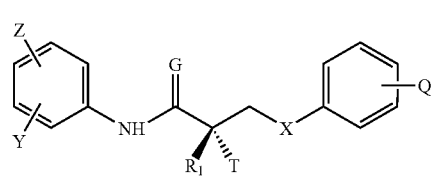

wherein

G is O or S;

X is a bond, O, $CH_2$, NH, Se, PR, NO or NR;

T is OH, OR, —$NHCOCH_3$, or NHCOR

Z is $NO_2$, CN, COOH, COR, NHCOR or CONHR;

Y is $CF_3$, F, I, Br, Cl, CN, $C(R)_3$ or $Sn(R)_3$;

Q is alkyl, halogen, $CF_3$, CN, $C(R)_3$, $Sn(R)_3$, $N(R)_2$, $NHCOCH_3$, $NHCOCF_3$, NHCOR, NHCONHR, NHCOOR, OCONHR, CONHR, $NHCSCH_3$, $NHCSCF_3$, NHCSR, $NHSO_2CH_3$, $NHSO_2R$, OR, COR, OCOR, $OSO_2R$, $SO_2R$, SR; or Q together with the benzene ring to which it is attached is a fused ring system represented by structure A, B or C:

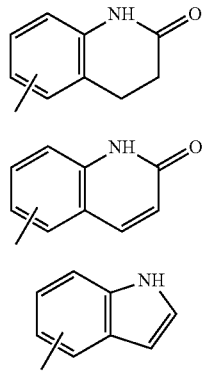

R is alkyl, haloalkyl, dihaloalkyl, trihaloalkyl, $CH_2F$, $CHF_2$, $CF_3$, $CF_2CF_3$, aryl, phenyl, halogen, alkenyl or OH; and $R_1$ is $CH_3$, $CH_2F$, $CHF_2$, $CF_3$, $CH_2CH_3$, or $CF_2CF_3$.

In one embodiment, the SARM is an analog of the compound of formula I. In another embodiment, the SARM is a derivative of the compound of formula I. In another embodiment, the SARM is an isomer of the compound of formula I. In another embodiment, the SARM is a metabolite of the compound of formula I. In another embodiment, the SARM is a pharmaceutically acceptable salt of the compound of formula I. In another embodiment, the SARM is a pharmaceutical product of the compound of formula I. In another embodiment, the SARM is a hydrate of the compound of formula I. In another embodiment, the SARM is an N-oxide of the compound of formula I. In another embodiment, the SARM is a combination of any of an analog, derivative, metabolite, isomer, pharmaceutically acceptable salt, pharmaceutical product, hydrate or N-oxide of the compound of formula I.

In one embodiment, the SARM compound is a compound of formula I wherein X is O. In one embodiment, the SARM compound is a compound of formula I wherein G is O. In another embodiment, the SARM compound is a compound of formula I wherein Z is $NO_2$. In another embodiment, the SARM compound is a compound of formula I wherein Z is CN. In another embodiment, the SARM compound is a compound of formula I wherein Y is $CF_3$. In another embodiment, the SARM compound is a compound of formula I wherein Q is $NHCOCH_3$. In another embodiment, the SARM compound is a compound of formula I wherein Q is F. In another embodiment, the SARM compound is a compound of formula I wherein T is OH. In another embodiment, the SARM compound is a compound of formula I wherein $R_1$ is $CH_3$.

In another embodiment, the SARM which: a) treats, prevents, inhibits, or suppresses BPH; and/or b) treats hair loss; and/or c) inhibits 5α-reductase enzyme; and/or d) antagonizes the androgen receptor is a compound represented by the structure of formula II.

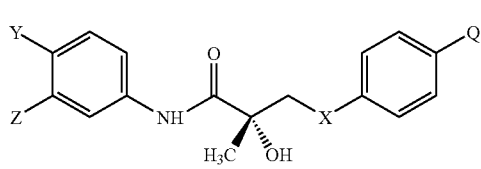

wherein

X is a bond, O, $CH_2$, NH, Se, PR, NO or NR;

Z is $NO_2$, CN, COOH, COR, NHCOR or CONHR;

Y is $CF_3$, F, I, Br, Cl, CN, $C(R)_3$ or $Sn(R)_3$;

Q is alkyl, halogen, $CF_3$, CN, $C(R)_3$, $Sn(R)_3$, $N(R)_2$, $NHCOCH_3$, $NHCOCF_3$, NHCOR, NHCONHR, NHCOOR, OCONHR, CONHR, $NHCSCH_3$, $NHCSCF_3$, NHCSR $NHSO_2CH_3$, $NHSO_2R$, OR, COR, OCOR, $OSO_2R$, $SO_2R$, SR; or Q together with the benzene ring to which it is attached is a fused ring system represented by structure A, B or C:

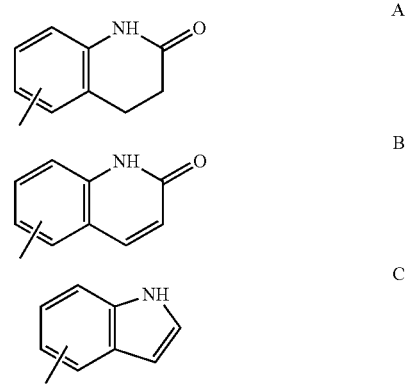

R is alkyl, haloalkyl, dihaloalkyl, trihaloalkyl, $CH_2F$, $CHF_2$, $CF_3$, $CF_2CF_3$, aryl, phenyl, halogen, alkenyl or OH.

In one embodiment, the SARM is an analog of the compound of formula II. In another embodiment, the SARM is a derivative of the compound of formula II. In another embodiment, the SARM is an isomer of the compound of formula II. In another embodiment, the SARM is a metabolite of the compound of formula II. In another embodiment, the SARM is a pharmaceutically acceptable salt of the compound of formula II. In another embodiment, the SARM is a pharmaceutical product of the compound of formula II. In another embodiment, the SARM is a hydrate of the compound of formula II. In another embodiment, the SARM is an N-oxide of the compound of formula II. In another embodiment, the SARM is a combination of any of an analog, derivative, metabolite, isomer, pharmaceutically acceptable salt, pharmaceutical product, hydrate or N-oxide of the compound of formula II.

In one embodiment, the SARM compound is a compound of formula II wherein X is O. In another embodiment, the SARM compound is a compound of formula II wherein Z is $NO_2$. In another embodiment, the SARM compound is a compound of formula II wherein Z is CN. In another embodiment, the SARM compound is a compound of formula II wherein Y is $CF_3$. In another embodiment, the SARM compound is a compound of formula II wherein Q is $NHCOCH_3$. In another embodiment, the SARM compound is a compound of formula II wherein Q is F.

In another embodiment, the SARM which: a) treats, prevents, inhibits, or suppresses BPH; and/or b) treats hair loss; and/or c) inhibits 5α-reductase enzyme; and/or d) antagonizes the androgen receptor is a compound represented by the structure of formula III.

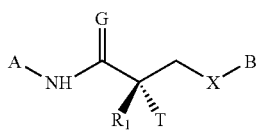

III wherein

X is a bond, O, CH$_2$, NH, Se, PR, NO or NR;

G is O or S;

R$_1$ is CH$_3$, CH$_2$F, CHF$_2$, CF$_3$, CH$_2$CH$_3$, or CF$_2$CF$_3$;

T is OH, OR, —NHCOCH$_3$, or NHCOR;

R is alkyl, haloalkyl, dihaloalkyl, trihaloalkyl, CH$_2$F, CHF$_2$, CF$_3$, CF$_2$CF$_3$, aryl, phenyl, halogen, alkenyl or OH;

A is a ring selected from:

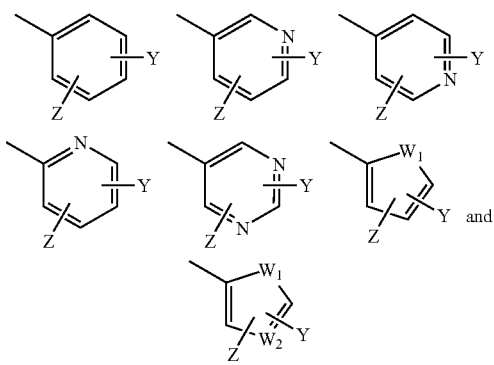

B is a ring selected from:

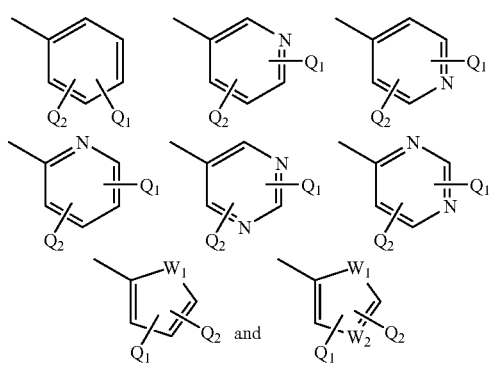

wherein

A and B cannot simultaneously be a benzene ring;

Z is NO$_2$, CN, COOH, COR, NHCOR or CONHR;

Y is CF$_3$, F, I, Br, Cl, CNCR$_3$ or SnR$_3$;

Q$_1$ and Q$_2$ are independently of each other a hydrogen, alkyl, halogen, CF$_3$, CN, C(R)$_3$, Sn(R)$_3$, N(R)$_2$, NHCOCH$_3$, NHCOCF$_3$, NHCOR, NHCONHR, NHCOOR, OCONHR, CONHR, NHCSCH$_3$, NHCSCF$_3$, NHCSR, NHSO$_2$CH$_3$, NHSO$_2$R, OR, COR, OCOR, OSO$_2$R, SO$_2$R, SR,

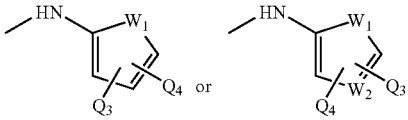

Q$_3$ and Q$_4$ are independently of each other a hydrogen, alkyl, halogen, CF$_3$, CN, C(R)$_3$, Sn(R)$_3$, N(R)$_2$, NHCOCH$_3$, NHCOCF$_3$, NHCOR, NHCONHR, NHCOOR, OCONHR, CONHR, NHCSCH$_3$, NHCSCF$_3$, NHCSR NHSO$_2$CH$_3$, NHSO$_2$R, OR, COR, OCOR, OSO$_2$R, SO$_2$R or SR;

W$_1$ is O, NH, NR, NO or S; and

W$_2$ is N or NO.

In one embodiment, the SARM is an analog of the compound of formula III. In another embodiment, the SARM is a derivative of the compound of formula III. In another embodiment, the SARM is an isomer of the compound of formula III. In another embodiment, the SARM is a metabolite of the compound of formula III. In another embodiment, the SARM is a pharmaceutically acceptable salt of the compound of formula III. In another embodiment, the SARM is a pharmaceutical product of the compound of formula III. In another embodiment, the SARM is a hydrate of the compound of formula III. In another embodiment, the SARM is an N-oxide of the compound of formula III. In another embodiment, the SARM is a combination of any of an analog, derivative, metabolite, isomer, pharmaceutically acceptable salt, pharmaceutical product, hydrate or N-oxide of the compound of formula III.

In one embodiment, the SARM compound is a compound of formula III wherein X is O. In another embodiment, the SARM compound is a compound of formula III wherein G is O. In another embodiment, the SARM compound is a compound of formula I wherein T is OH. In another embodiment, the SARM compound is a compound of formula III wherein R$_1$ is CH$_3$. In another embodiment, the SARM compound is a compound of formula III wherein Z is NO$_2$. In another embodiment, the SARM compound is a compound of formula III wherein Z is CN. In another embodiment, the SARM compound is a compound of formula III wherein Y is CF$_3$. In another embodiment, the SARM compound is a compound of formula III wherein Q$_1$ is NHCOCH$_3$. In another embodiment, the SARM compound is a compound of formula III wherein Q$_1$ is F.

The substituents Z and Y can be in any position of the ring carrying these substituents (hereinafter "A ring"). In one embodiment, the substituent Z is in the para position of the A ring. In another embodiment, the substituent Y is in the meta position of the A ring. In another embodiment, the substituent Z is in the para position of the A ring and substituent Y is in the meta position of the A ring.

The substituents Q$_1$ and Q$_2$ can be in any position of the ring carrying these substituents (hereinafter "B ring"). In one embodiment, the substitutent Q$_1$ is in the para position of the B ring. In another embodiment, the substituent is Q$_2$ is H. In another embodiment, the substitutent Q$_1$ is in the para position of the B ring and the substituent is Q$_2$ is H. In another embodiment, the substitutent Q$_1$ is NHCOCH$_3$ and is in the para position of the B ring, and the substituent is Q$_2$ is H.

In another embodiment, the SARM which: a) treats, prevents, inhibits, or suppresses BPH; and/or b) treats hair loss; and/or c) inhibits 5α-reductase enzyme; and/or d) antagonizes the androgen receptor is a compound represented by the structure of formula IV.

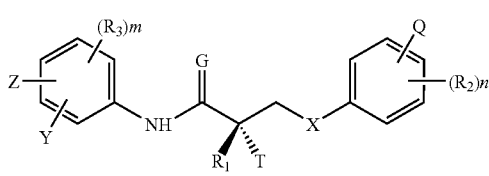

IV wherein
X is a bond, O, CH₂, NH, Se, PR, NO or NR;
G is O or S;
T is OH, OR, —NHCOCH₃, or NHCOR;
R is alkyl, haloalkyl, dihaloalkyl, trihaloalkyl, CH₂F, CHF₂, CF₃, CF₂CF₃, aryl, phenyl, halogen, alkenyl or OH;
R₁ is CH₃, CH₂F, CHF₂, CF₃, CH₂CH₃, or CF₂CF₃;
R₂ is F, Cl, Br, I, CH₃, CF₃, OH, CN, NO₂, NHCOCH₃, NHCOCF₃, NHCOR, alkyl, arylalkyl, OR, NH₂, NHR, N(R)₂, SR;
R₃ is F, Cl, Br, I, CN, NO₂, COR, COOH, CONHR, CF₃, SnR₃, or R₃ together with the benzene ring to which it is attached forms a fused ring system represented by the structure:

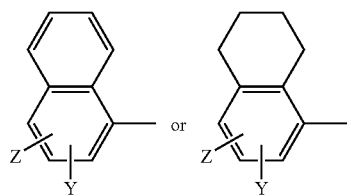

Z is NO₂, CN, COR, COOH, or CONHR;
Y is CF₃, F, Br, Cl, I, CN, or Sn(R)₃;
Q is H, alkyl, halogen, CF₃, CN, C(R)₃, Sn(R)₃, N(R)₂, NHCOCH₃, NHCOCF₃, NHCOR, NHCONHR, NHCOOR, OCONHR, CONHR, NHCSCH₃, NHCSCF₃, NHCSR NHSO₂CH₃, NHSO₂R, OH, OR, COR, OCOR, OSO₂R, SO₂R, SR; or Q together with the benzene ring to which it is attached is a fused ring system represented by structure A, B or C:

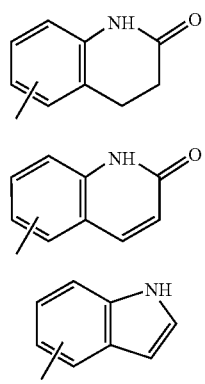

n is an integer of 1-4; and
m is an integer of 1-3.

In one embodiment, the SARM is an analog of the compound of formula IV. In another embodiment, the SARM is a derivative of the compound of formula IV. In another embodiment, the SARM is an isomer of the compound of formula IV. In another embodiment, the SARM is a metabolite of the compound of formula IV. In another embodiment, the SARM is a pharmaceutically acceptable salt of the compound of formula IV. In another embodiment, the SARM is a pharmaceutical product of the compound of formula IV. In another embodiment, the SARM is a hydrate of the compound of formula IV. In another embodiment, the SARM is an N-oxide of the compound of formula IV. In another embodiment, the SARM is a combination of any of an analog, derivative, metabolite, isomer, pharmaceutically acceptable salt, pharmaceutical product, hydrate or N-oxide of the compound of formula IV.

In one embodiment, the SARM compound is a compound of formula IV wherein X is O. In another embodiment, the SARM compound is a compound of formula IV wherein G is O. In another embodiment, the SARM compound is a compound of formula IV wherein Z is NO₂. In another embodiment, the SARM compound is a compound of formula IV wherein Z is CN. In another embodiment, the SARM compound is a compound of formula IV wherein Y is CF₃. In another embodiment, the SARM compound is a compound of formula IV wherein Q is NHCOCH₃. In another embodiment, the SARM compound is a compound of formula IV wherein Q is F. In another embodiment, the SARM compound is a compound of formula IV wherein T is OH. In another embodiment, the SARM compound is a compound of formula IV wherein R₁ is CH₃. In another embodiment, the SARM compound is a compound of formula IV wherein Q is F and R₂ is CH₃. In another embodiment, the SARM compound is a compound of formula IV wherein Q is F and R₂ is Cl.

The substituents Z, Y and R₃ can be in any position of the ring carrying these substituents (hereinafter "A ring"). In one embodiment, the substituent Z is in the para position of the A ring. In another embodiment, the substituent Y is in the meta position of the A ring. In another embodiment, the substituent Z is in the para position of the A ring and substituent Y is in the meta position of the A ring.

The substituents Q and R₂ can be in any position of the ring carrying these substituents (hereinafter "B ring"). In one embodiment, the substitutent Q is in the para position of the B ring. In another embodiment, the substitutent Q is in the para position of the B ring. In another embodiment, the substitutent Q is NHCOCH₃ and is in the para position of the B ring.

As contemplated herein, when the integers m and n are greater than one, the substituents R₂ and R₃ are not limited to one particular substituent, and can be any combination of the substituents listed above.

In another embodiment, the SARM which: a) treats, prevents, inhibits, or suppresses BPH; and/or b) treats hair loss; and/or c) inhibits 5-reductase enzyme; and/or d) antagonizes the androgen receptor is a compound represented by the structure of formula V.

V

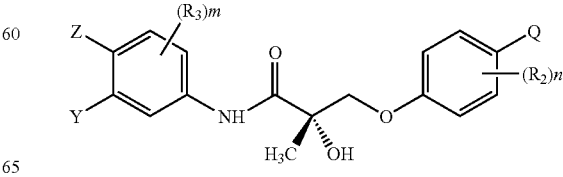

wherein

R$_2$ is F, Cl, Br, I, CH$_3$, CF$_3$, OH, CN, NO$_2$, NHCOCH$_3$, NHCOCF$_3$, NHCOR, alkyl, arylalkyl, OR, NH$_2$, NHR, N(R)$_2$, SR;

R$_3$ is F, Cl, Br, I, CN, NO$_2$, COR, COOH, CONHR, CF$_3$, SnR$_3$, or R$_3$ together with the benzene ring to which it is attached forms a fused ring system represented by the structure:

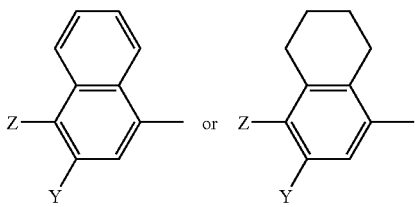

R is alkyl, haloalkyl, dihaloalkyl, trihaloalkyl, CH$_2$F, CHF$_2$, CF$_3$, CF$_2$CF$_3$, aryl, phenyl, halogen, alkenyl or OH;

Z is NO$_2$, CN, COR, COOH, or CONHR;

Y is CF$_3$, F, Br, Cl, I, CN, or Sn(R)$_3$;

Q is H, alkyl, halogen, CF$_3$, CN, C(R)$_3$, Sn(R)$_3$, N(R)$_2$, NHCOCH$_3$, NHCOCF$_3$, NHCOR, NHCONHR, NHCOOR, OCONHR, CONHR, NHCSCH$_3$, NHCSCF$_3$, NHCSR, NHSO$_2$CH$_3$, NHSO$_2$R, OH, OR, COR, OCOR, OSO$_2$R, SO$_2$R, SR; or Q together with the benzene ring to which it is attached is a fused ring system represented by structure A, B or C:

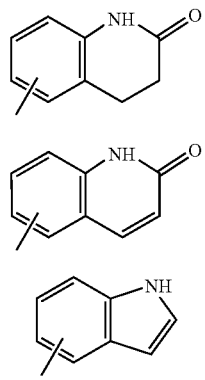

n is an integer of 1-4; and
m is an integer of 1-3.

In one embodiment, the SARM is an analog of the compound of formula V. In another embodiment, the SARM is a derivative of the compound of formula V. In another embodiment, the SARM is an isomer of the compound of formula V. In another embodiment, the SARM is a metabolite of the compound of formula V. In another embodiment, the SARM is a pharmaceutically acceptable salt of the compound of formula V. In another embodiment, the SARM is a pharmaceutical product of the compound of formula V. In another embodiment, the SARM is a hydrate of the compound of formula V. In another embodiment, the SARM is an N-oxide of the compound of formula V. In another embodiment, the SARM is a combination of any of an analog, derivative, metabolite, isomer, pharmaceutically acceptable salt, pharmaceutical product, hydrate or N-oxide of the compound of formula V.

In another embodiment, the SARM is a compound of formula V wherein Z is NO$_2$. In another embodiment, the SARM is a compound of formula V wherein Z is CN. In another embodiment, the SARM is a compound of formula V wherein Y is CF$_3$. In another embodiment, the SARM is a compound of formula V wherein Q is NHCOCH$_3$. In another embodiment, the SARM is a compound of formula V wherein Q is F. In another embodiment, the SARM is a compound of formula V wherein Q is F and R$_2$ is CH$_3$. In another embodiment, the SARM is a compound of formula V wherein Q is F and R$_2$ is Cl.

The substituents Z, Y and R$_3$ can be in any position of the A ring, and the substituents Q and R$_2$ can be in any position of B ring, as discussed above for compound IV. Furthermore, as discussed above, when the integers m and n are greater than one, the substituents R$_2$ and R$_3$ are not limited to one particular substituent, and can be any combination of the substituents listed above.

In another embodiment, the SARM which: a) treats, prevents, inhibits, or suppresses BPH; and/or b) treats hair loss; and/or c) inhibits 5α-reductase enzyme; and/or d) antagonizes the androgen receptor is a compound represented by the structure of formula VI.

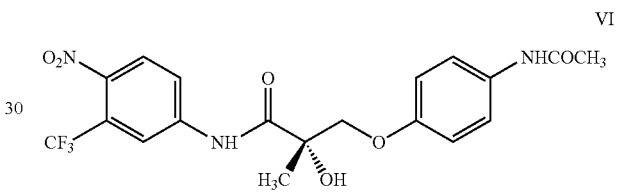

In one embodiment, the SARM is an analog of the compound of formula VI. In another embodiment, the SARM is a derivative of the compound of formula VI. In another embodiment, the SARM is an isomer of the compound of formula VI. In another embodiment, the SARM is a metabolite of the compound of formula VI. In another embodiment, the SARM is a pharmaceutically acceptable salt of the compound of formula VI. In another embodiment, the SARM is a pharmaceutical product of the compound of formula VI. In another embodiment, the SARM is a hydrate of the compound of formula VI. In another embodiment, the SARM is an N-oxide of the compound of formula VI. In another embodiment, the SARM is a combination of any of an analog, derivative, metabolite, isomer, pharmaceutically acceptable salt, pharmaceutical product, hydrate or N-oxide of the compound of formula VI.

In another embodiment, the SARM which: a) treats, prevents, inhibits, or suppresses BPH; and/or b) treats hair loss; and/or c) inhibits 5α-reductase enzyme; and/or d) antagonizes the androgen receptor is a compound represented by the structure of formula VII.

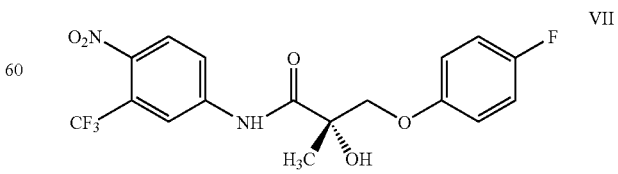

In one embodiment, the SARM is an analog of the compound of formula VII. In another embodiment, the SARM is a derivative of the compound of formula VII. In another embodiment, the SARM is an isomer of the compound of formula VII. In another embodiment, the SARM is a metabolite of the compound of formula VII. In another embodiment, the SARM is a pharmaceutically acceptable salt of the compound of formula VII. In another embodiment, the SARM is a pharmaceutical product of the compound of formula VII. In another embodiment, the SARM is a hydrate of the compound of formula VII. In another embodiment, the SARM is an N-oxide of the compound of formula VII. In another embodiment, the SARM is a combination of any of an analog, derivative, metabolite, isomer, pharmaceutically acceptable salt, pharmaceutical product, hydrate or N-oxide of the compound of formula VII.

In one embodiment, the SARM which: a) treats, prevents, inhibits, or suppresses BPH; and/or b) treats hair loss; and/or c) inhibits 5α-reductase enzyme; and/or d) antagonizes the androgen receptor is a compound represented by the structure of formula VIII.

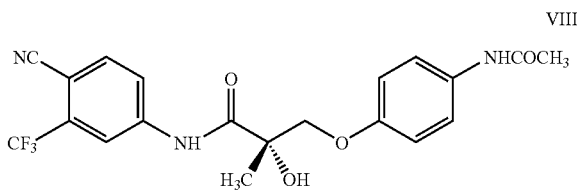

VIII

In one embodiment, the SARM is an analog of the compound of formula VIII. In another embodiment, the SARM is a derivative of the compound of formula VIII. In another embodiment, the SARM is an isomer of the compound of formula VIII. In another embodiment, the SARM is a metabolite of the compound of formula VIII. In another embodiment, the SARM is a pharmaceutically acceptable salt of the compound of formula VIII. In another embodiment, the SARM is a pharmaceutical product of the compound of formula VIII. In another embodiment, the SARM is a hydrate of the compound of formula VIII. In another embodiment, the SARM is an N-oxide of the compound of formula VIII. In another embodiment, the SARM is a combination of any of an analog, derivative, metabolite, isomer, pharmaceutically acceptable salt, pharmaceutical product, hydrate or N-oxide of the compound of formula VIII.

In one embodiment, the SARM which: a) treats, prevents, inhibits, or suppresses BPH; and/or b) treats hair loss; and/or c) inhibits 5α-reductase enzyme; and/or d) antagonizes the androgen receptor is a compound represented by the structure of formula IX.

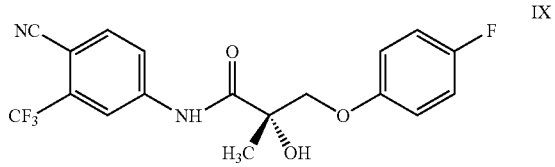

IX

In one embodiment, the SARM is an analog of the compound of formula IX. In another embodiment, the SARM is a derivative of the compound of formula IX. In another embodiment, the SARM is an isomer of the compound of formula IX. In another embodiment, the SARM is a metabolite of the compound of formula IX. In another embodiment, the SARM is a pharmaceutically acceptable salt of the compound of formula IX. In another embodiment, the SARM is a pharmaceutical product of the compound of formula IX. In another embodiment, the SARM is a hydrate of the compound of formula IX. In another embodiment, the SARM is an N-oxide of the compound of formula IX. In another embodiment, the SARM is a combination of any of an analog, derivative, metabolite, isomer, pharmaceutically acceptable salt, pharmaceutical product, hydrate or N-oxide of the compound of formula IX.

The substituent R in formulas (I) and (II) is defined herein as an alkyl, haloalkyl, dihaloalkyl, trihaloalkyl, $CH_2F$, $CHF_2$, $CF_3$, $CF_2CF_3$, aryl, phenyl, halogen, alkenyl or OH.

An "alkyl" group refers to a saturated aliphatic hydrocarbon, including straight-chain, branched-chain and cyclic alkyl groups. In one embodiment, the alkyl group has 1-12 carbons. In another embodiment, the alkyl group has 1-7 carbons. In another embodiment, the alkyl group has 1-6 carbons. In another embodiment, the alkyl group has 1-4 carbons. The alkyl group may be unsubstituted or substituted by one or more groups selected from halogen, hydroxy, alkoxy carbonyl, amido, alkylamido, dialkylamido, nitro, amino, alkylamino, dialkylamino, carboxyl, thio and thioalkyl.

An "alkenyl" group refers to an unsaturated hydrocarbon, including straight chain, branched chain and cyclic groups having one or more double bond. The alkenyl group may have one double bond, two double bonds, three double bonds etc. Examples of alkenyl groups are ethenyl, propenyl, butenyl, cyclohexenyl etc. The alkenyl group may be unsubstituted or substituted by one or more groups selected from halogen, hydroxy, alkoxy carbonyl, amido, alkylamido, dialkylamido, nitro, amino, alkylamino, dialkylamino, carboxyl, thio and thioalkyl.

A "haloalkyl" group refers to an alkyl group as defined above, which is substituted by one or more halogen atoms, e.g. by F, Cl, Br or I.

An "aryl" group refers to an aromatic group having at least one carbocyclic aromatic group or heterocyclic aromatic group, which may be unsubstituted or substituted by one or more groups selected from halogen, haloalkyl, hydroxy, alkoxy carbonyl, amido, alkylamido, dialkylamido, nitro, amino, alkylamino, dialkylamino, carboxy or thio or thioalkyl. Nonlimiting examples of aryl rings are phenyl, naphthyl, pyranyl, pyrrolyl, pyrazinyl, pyrimidinyl, pyrazolyl, pyridinyl, furanyl, thiophenyl, thiazolyl, imidazolyl, isoxazolyl, and the like.

A "hydroxyl" group refers to an OH group. An "alkenyl" group refers to a group having at least one carbon to carbon double bond. A halo group refers to F, Cl, Br or I.

An "arylalkyl" group refers to an alkyl bound to an aryl, wherein alkyl and aryl are as defined above. An example of an arylalkyl group is a benzyl group.

As contemplated herein, this invention provides a method of treating, preventing, suppressing, inhibiting or reducing the incidence of benign prostate hyperplasia in a male subject, by administering to the subject a selective androgen receptor modulator (SARM). In another embodiment, the method includes administering an analog of said SARM. In another embodiment, the method includes administering a derivative of said SARM. In another embodiment, the method includes administering an isomer of said SARM. In another embodiment, the method includes administering a metabolite of said SARM. In another embodiment, the method includes administering a pharmaceutically acceptable salt of said SARM. In another embodiment, the method includes administering a hydrate of said SARM. In another embodiment, the method includes administering an N-oxide of said SARM. In another embodiment, the method includes administering a pharmaceutical product of said SARM.

As defined herein, the term "isomer" includes, but is not limited to optical isomers and analogs, structural isomers and analogs, conformational isomers and analogs, and the like.

In one embodiment, this invention encompasses the use of different optical isomers of the SARM compound. It will be appreciated by those skilled in the art that the SARMs of the present invention contain at least one chiral center. Accordingly, the SARMs used in the methods of the present invention may exist in, and be isolated in, optically-active or racemic forms. Some compounds may also exhibit polymorphism. It is to be understood that the present invention encompasses any racemic, optically-active, polymorphic, or stereroisomeric form, or any combination thereof, which form possesses properties useful in the treatment of BPH described herein. In one embodiment, the SARMs are the pure (R)-isomers. In another embodiment, the SARMs are the pure (S)-isomers. In another embodiment, the SARMs are a mixture of the (R) and the (S) isomers. In another embodiment, the SARMs are a racemic mixture comprising an equal amount of the (R) and the (S) isomers. It is well known in the art how to prepare optically-active forms (for example, by resolution of the racemic form by recrystallization techniques, by synthesis from optically-active starting materials, by chiral synthesis, or by chromatographic separation using a chiral stationary phase).

The invention includes pharmaceutically acceptable salts of amino-substituted compounds with organic and inorganic acids, for example, citric acid and hydrochloric acid. The invention also includes N-oxides of the amino substituents of the compounds described herein. Pharmaceutically acceptable salts can also be prepared from the phenolic compounds by treatment with inorganic bases, for example, sodium hydroxide. Also, esters of the phenolic compounds can be made with aliphatic and aromatic carboxylic acids, for example, acetic acid and benzoic acid esters.

This invention further includes derivatives of the SARM compounds. The term "derivative" includes but is not limited to ether derivatives, acid derivatives, amide derivatives, acid derivatives, ester derivatives and the likes. In addition, this invention further includes hydrates of the SARM compounds. The term "hydrate" includes but is not limited to hemihydrate, monohydrate, dihydrate, trihydrate and the like.

This invention further includes metabolites of the SARM compounds. The term "metabolite" means any substance produced from another substance by metabolism or a metabolic process.

This invention further includes pharmaceutical products of the SARM compounds. The term "pharmaceutical product" means a composition suitable for pharmaceutical use (pharmaceutical composition), as defined herein.

Biological Activity of Selective Androgen Modulator Compounds

As contemplated herein, the SARMs which are useful in preventing and treating BPH are classified as androgen receptor agonists (AR agonists) or androgen receptor antagonists (AR antagonists).

The AR is a ligand-activated transcriptional regulatory protein that mediates induction of male sexual development and function through its activity with endogenous androgens (male sex hormones). The androgenic hormones are steroids which are produced in the body by the testis and the cortex of the adrenal gland. Androgenic steroids play an important role in many physiologic processes, including the development and maintenance of male sexual characteristics such as muscle and bone mass, prostate growth, spermatogenesis, and the male hair pattern (Matsumoto, Endocrinol. Met. Clin. N. Am. 23:857-75 (1994)). The endogenous steroidal androgens include testosterone and dihydrotestosterone ("DHT"). Other steroidal androgens include esters of testosterone, such as the cypionate, propionate, phenylpropionate, cyclopentylpropionate, isocarporate, enanthate, and decanoate esters, and other synthetic androgens such as 7-Methyl-Nortestosterone ("MENT") and its acetate ester (Sundaram et al., "7 Alpha-Methyl-Nortestosterone (MENT): The Optimal Androgen For Male Contraception," Ann. Med., 25:199-205 (1993) ("Sundaram")).

A receptor agonist is a substance which binds receptors and activates them. A receptor antagonist is a substance which binds receptors and inactivates them. In one embodiment, the SARMs which are useful in treating and preventing BPH are AR agonists, and are, therefore, useful in binding to and activating the AR. In another embodiment, the SARMs which are useful in treating and preventing BPH are AR antagonists, and are, therefore, useful in binding to and inactivating the AR. Assays to determine whether the compounds of the present invention are AR agonists or antagonists are well known to a person skilled in the art. For example, AR agonistic activity can be determined by monitoring the ability of the SARM compounds to maintain and/or stimulate the growth of AR containing tissue such as prostate and seminal vesicles, as measured by weight. AR antagonistic activity can be determined by monitoring the ability of the SARM compounds inhibit the growth of AR containing tissue.

In yet another embodiment, the SARM compounds of the present invention can be classified as partial AR agonist/antagonists. The SARMs are AR agonists in some tissues, to cause increased transcription of AR-responsive genes (e.g. muscle anabolic effect). In other tissues, these compounds serve as competitive inhibitors of testosterone/DHT on the AR to prevent agonistic effects of the native androgens.

The compounds of the present invention bind either reversibly or irreversibly to the androgen receptor. In one embodiment, the SARM compounds bind reversibly to the androgen receptor. In another embodiment, the SARM compounds bind irreversibly to the androgen receptor. The compounds of the present invention may contain a functional group (affinity label) that allows alkylation of the androgen receptor (i.e. covalent bond formation). Thus, in this case, the compounds bind irreversibly to the receptor and, accordingly, cannot be displaced by a steroid, such as the endogenous ligands DHT and testosterone.

As demonstrated herein, the SARM compounds of the present invention are potent inhibitors of a 5-α reductase enzyme. Thus, in one embodiment, this invention provides a method of inhibiting a 5-α reductase enzyme, comprising contacting the enzyme with an effective 5-α reductase inhibitory amount of a selective androgen receptor modulator (SARM) and/or its analog, derivative, isomer, metabolite, pharmaceutically acceptable salt, pharmaceutical product, hydrate, N-oxide, or any combination thereof, as described herein. In one embodiment, the SARM compound that is shown to be a potent inhibitor of a 5-α reductase enzyme is a compound of formula I. In another embodiment, the SARM compound that is shown to be a potent inhibitor of a 5-α reductase enzyme is a compound of formula II. In another embodiment, the SARM compound that is shown to be a potent inhibitor of a 5-α reductase enzyme is a compound of formula III. In another embodiment, the SARM compound that is shown to be a potent inhibitor of a 5-α reductase enzyme is a compound of formula IV. In another embodiment, the SARM compound that is shown to be a potent inhibitor of a 5-α reductase enzyme is a compound of formula V. In another embodiment, the SARM compound that is shown to be a potent inhibitor of a 5-α reductase enzyme is a compound of formula VI. In another embodiment, the SARM compound that is shown to be a potent inhibitor of a 5-α reductase enzyme is a compound of formula VII.

In another embodiment, the SARM compound that is shown to be a potent inhibitor of a 5-α reductase enzyme is a compound of formula VIII. In another embodiment, the SARM compound that is shown to be a potent inhibitor of a 5-α reductase enzyme is a compound of formula IXI.

In one embodiment of the present invention, the 5-α reductase enzyme is a testosterone 5-α reductase enzyme. A testosterone 5-α reductase enzyme is an enzyme which converts testosterone (T) to dihydrotestosterone (DHT). DHT, which binds with five-fold greater affinity to the human androgen receptor, is thought to be the mediator of androgen effects in many tissues. DHT causes proliferation of the prostatic tissue, and excessive DHT levels are accompanied by excessive cellular proliferation, which is in turn accompanied by prostate enlargement. By inhibition of testosterone 5-α reductase with the SARM compounds of the present invention, the formation of DHT could be curtailed and, it is hoped, prostate enlargement can be blocked.

There are two isoforms of 5-α reductase—type 1 isozyme expressed predominantly in the liver and skin, and type-2 isozyme expressed predominantly in the prostate. As demonstrated herein, the SARMs of the present invention are effective in inhibiting both type 1 and type 2 5-α reductase. Thus, in one embodiment, the SARM compound that is shown to be a potent inhibitor of 5-α reductase enzyme is potent inhibitor of 5-α reductase enzyme type 1. In another embodiment, the SARM compound that is shown to be a potent inhibitor of 5-α reductase enzyme is potent inhibitor of 5-α reductase enzyme type 2.

In another embodiment, as demonstrated herein, the SARM compound that is shown to be a potent inhibitor of 5-α reductase enzyme is a competitive inhibitor of the 5-α reductase enzyme.

As defined herein, "contacting" means that the SARM compound of the present invention is introduced into a sample containing the enzyme in a test tube, flask, tissue culture, chip, array, plate, microplate, capillary, or the like, and incubated at a temperature and time sufficient to permit binding of the SARM to the enzyme. Methods for contacting the samples with the SARM or other specific binding components are known to those skilled in the art and may be selected depending on the type of assay protocol to be run. Incubation methods are also standard and are known to those skilled in the art.

In another embodiment, the term "contacting" means that the SARM compound of the present invention is introduced into a subject receiving treatment, and the SARM compound is allowed to come in contact with the androgen receptor in-vivo.

As described above, the androgenic hormones such as testosterone and DHT play an important role in many physiologic processes, including the development and maintenance of the male hair pattern. As demonstrated herein, inhibition of 5-α reductase inhibitor by the SARM compounds of the present invention affects male hair loss. This invention thus provides a method of treating a subject suffering from hair loss, comprising the step of administering to the subject a therapeutically effective amount of a 5-α reductase inhibitor, wherein said inhibitor is a selective androgen receptor modulator (SARM) and/or its analog, derivative, isomer, metabolite, pharmaceutically acceptable salt, pharmaceutical product, hydrate, N-oxide, or any combination thereof as described herein.

As used herein, the term "treating" includes disorder remitative treatment.

This invention provides the use of a composition and a pharmaceutical composition for treating, preventing, suppressing, inhibiting or reducing the incidence of benign prostate hyperplasia in a male subject, the composition comprising a selective androgen receptor modulator (SARM) and/or its analog, derivative, isomer, metabolite, pharmaceutically acceptable salt, pharmaceutical product, hydrate, N-oxide, or any combination thereof as described herein, in a pharmaceutical preparation further comprising a suitable carrier or diluent.

This invention further provides the use of a composition and a pharmaceutical composition for treating a subject suffering from hair loss, the composition comprising a therapeutically effective amount of a 5-α reductase inhibitor, wherein the inhibitor is a selective androgen receptor modulator (SARM) and/or its analog, derivative, isomer, metabolite, pharmaceutically acceptable salt, pharmaceutical product, hydrate, N-oxide, or any combination thereof as described herein.

The present invention provides a safe and effective method for treating, preventing, suppressing, inhibiting or reducing BPH and is particularly useful for relieving symptoms and signs associated with BPH in a subject suffering from BPH. The present invention further provides a safe and effective method for treating hair loss in a subject suffering from hair loss. In one embodiment, the subject is a mammalian subject. In another embodiment, the subject is a human subject. In another embodiment, the subject is a male subject.

Pharmaceutical Compositions

As used herein, "pharmaceutical composition" means a "therapeutically effective amount" of the active ingredient, i.e. the SARM compound, together with a pharmaceutically acceptable carrier or diluent. A "therapeutically effective amount" as used herein refers to that amount which provides a therapeutic effect for a given condition and administration regimen.

The pharmaceutical compositions containing the SARM agent can be administered to a subject by any method known to a person skilled in the art, such as parenterally, paracancerally, transmucosally, transdermally, intramuscularly, intravenously, intradermally, subcutaneously, intraperitonealy, intraventricularly, intracranially, intravaginally or intratumorally.

In one embodiment, the pharmaceutical compositions are administered orally, and are thus formulated in a form suitable for oral administration, i.e. as a solid or a liquid preparation. Suitable solid oral formulations include tablets, capsules, pills, granules, pellets and the like. Suitable liquid oral formulations include solutions, suspensions, dispersions, emulsions, oils and the like. In one embodiment of the present invention, the SARM compounds are formulated in a capsule. In accordance with this embodiment, the compositions of the present invention comprise in addition to the SARM active compound and the inert carrier or diluent, a hard gelating capsule.

Further, in another embodiment, the pharmaceutical compositions are administered by intravenous, intraarterial, or intramuscular injection of a liquid preparation. Suitable liquid formulations include solutions, suspensions, dispersions, emulsions, oils and the like.

In one embodiment, the pharmaceutical compositions are administered intravenously, and are thus formulated in a form suitable for intravenous administration. In another embodiment, the pharmaceutical compositions are administered intraarterially, and are thus formulated in a form suitable for intraarterial administration. In another embodiment, the pharmaceutical compositions are administered intramuscularly, and are thus formulated in a form suitable for intramuscular administration.

Further, in another embodiment, the pharmaceutical compositions are administered topically to body surfaces, and are thus formulated in a form suitable for topical administration. Suitable topical formulations include gels, ointments, creams, lotions, drops and the like. For topical administration, the SARM agents or their physiologically tolerated derivatives such as salts, esters, N-oxides, and the like are prepared and applied as solutions, suspensions, or emulsions in a physiologically acceptable diluent with or without a pharmaceutical carrier.

Further, in another embodiment, the pharmaceutical compositions are administered as a suppository, for example a rectal suppository or a urethral suppository. Further, in another embodiment, the pharmaceutical compositions are administered by subcutaneous implantation of a pellet. In a further embodiment, the pellet provides for controlled release of SARM agent over a period of time.

In another embodiment, the active compound can be delivered in a vesicle, in particular a liposome (see Langer, Science 249:1527-1533 (1990); Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid).

As used herein "pharmaceutically acceptable carriers or diluents" are well known to those skilled in the art. The carrier or diluent may be a solid carrier or diluent for solid formulations, a liquid carrier or diluent for liquid formulations, or mixtures thereof.

Solid carriers/diluents include, but are not limited to, a gum, a starch (e.g. corn starch, pregeletanized starch), a sugar (e.g., lactose, mannitol, sucrose, dextrose), a cellulosic material (e.g. microcrystalline cellulose), an acrylate (e.g. polymethylacrylate), calcium carbonate, magnesium oxide, talc, or mixtures thereof.

For liquid formulations, pharmaceutically acceptable carriers may be aqueous or non-aqueous solutions, suspensions, emulsions or oils. Examples of non-aqueous solvents are propylene glycol, polyethylene glycol, and injectable organic esters such as ethyl oleate. Aqueous carriers include water, alcoholic/aqueous solutions, emulsions or suspensions, including saline and buffered media. Examples of oils are those of petroleum, animal, vegetable, or synthetic origin, for example, peanut oil, soybean oil, mineral oil, olive oil, sunflower oil, and fish-liver oil.

Parenteral vehicles (for subcutaneous, intravenous, intraarterial, or intramuscular injection) include sodium chloride solution, Ringer's dextrose, dextrose and sodium chloride, lactated Ringer's and fixed oils. Intravenous vehicles include fluid and nutrient replenishers, electrolyte replenishers such as those based on Ringer's dextrose, and the like. Examples are sterile liquids such as water and oils, with or without the addition of a surfactant and other pharmaceutically acceptable adjuvants. In general, water, saline, aqueous dextrose and related sugar solutions, and glycols such as propylene glycols or polyethylene glycol are preferred liquid carriers, particularly for injectable solutions. Examples of oils are those of petroleum, animal, vegetable, or synthetic origin, for example, peanut oil, soybean oil, mineral oil, olive oil, sunflower oil, and fish-liver oil.

In addition, the compositions may further comprise binders (e.g. acacia, cornstarch, gelatin, carbomer, ethyl cellulose, guar gum, hydroxypropyl cellulose, hydroxypropyl methyl cellulose, povidone), disintegrating agents (e.g. cornstarch, potato starch, alginic acid, silicon dioxide, croscarmelose sodium, crospovidone, guar gum, sodium starch glycolate), buffers (e.g., Tris-HCl., acetate, phosphate) of various pH and ionic strength, additives such as albumin or gelatin to prevent absorption to surfaces, detergents (e.g., Tween 20, Tween 80, Pluronic F68, bile acid salts), protease inhibitors, surfactants (e.g. sodium lauryl sulfate), permeation enhancers, solubilizing agents (e.g., glycerol, polyethylene glycerol), anti-oxidants (e.g., ascorbic acid, sodium metabisulfite, butylated hydroxyanisole), stabilizers (e.g. hydroxypropyl cellulose, hyroxypropylmethyl cellulose), viscosity increasing agents (e.g. carbomer, colloidal silicon dioxide, ethyl cellulose, guar gum), sweetners (e.g. aspartame, citric acid), preservatives (e.g., Thimerosal, benzyl alcohol, parabens), lubricants (e.g. stearic acid, magnesium stearate, polyethylene glycol, sodium lauryl sulfate), flow-aids (e.g. colloidal silicon dioxide), plasticizers (e.g. diethyl phthalate, triethyl citrate), emulsifiers (e.g. carbomer, hydroxypropyl cellulose, sodium lauryl sulfate), polymer coatings (e.g., poloxamers or poloxamines), coating and film forming agents (e.g. ethyl cellulose, acrylates, polymethacrylates) and/or adjuvants.

In one embodiment, the pharmaceutical compositions provided herein are controlled release compositions, i.e. compositions in which the SARM compound is released over a period of time after administration. Controlled or sustained release compositions include formulation in lipophilic depots (e.g. fatty acids, waxes, oils). In another embodiment, the composition is an immediate release composition, i.e. a composition in which all of the SARM compound is released immediately after administration.

In yet another embodiment, the pharmaceutical composition can be delivered in a controlled release system. For example, the agent may be administered using intravenous infusion, an implantable osmotic pump, a transdermal patch, liposomes, or other modes of administration. In one embodiment, a pump may be used (see Langer, supra; Sefton, CRC Crit. Ref. Biomed. Eng. 14:201 (1987); Buchwald et al., Surgery 88:507 (1980); Saudek et al., N. Engl. J. Med. 321: 574 (1989). In another embodiment, polymeric materials can be used. In yet another embodiment, a controlled release system can be placed in proximity to the therapeutic target, i.e., the brain, thus requiring only a fraction of the systemic dose (see, e.g., Goodson, in Medical Applications of Controlled Release, supra, vol. 2, pp. 115-138 (1984). Other controlled release systems are discussed in the review by Langer (Science 249:1527-1533 (1990).

The compositions may also include incorporation of the active material into or onto particulate preparations of polymeric compounds such as polylactic acid, polglycolic acid, hydrogels, etc, or onto liposomes, microemulsions, micelles, unilamellar or multilamellar vesicles, erythrocyte ghosts, or spheroplasts.) Such compositions will influence the physical state, solubility, stability, rate of in vivo release, and rate of in vivo clearance.

Also comprehended by the invention are particulate compositions coated with polymers (e.g. poloxamers or poloxamines) and the compound coupled to antibodies directed against tissue-specific receptors, ligands or antigens or coupled to ligands of tissue-specific receptors.

Also comprehended by the invention are compounds modified by the covalent attachment of water-soluble polymers such as polyethylene glycol, copolymers of polyethylene glycol and polypropylene glycol, carboxymethyl cellulose, dextran, polyvinyl alcohol, polyvinylpyrrolidone or polyproline. The modified compounds are known to exhibit substantially longer half-lives in blood following intravenous injection than do the corresponding unmodified compounds (Abuchowski et al., 1981; Newmark et al., 1982; and Katre et al., 1987). Such modifications may also increase the compound's solubility in aqueous solution, eliminate aggregation, enhance the physical and chemical stability of the compound, and greatly reduce the immunogenicity and reactivity of the compound. As a result, the desired in vivo biological activity may be achieved by the administration of such polymer-compound abducts less frequently or in lower doses than with the unmodified compound.

The preparation of pharmaceutical compositions which contain an active component is well understood in the art, for example by mixing, granulating, or tablet-forming processes. The active therapeutic ingredient is often mixed with excipients which are pharmaceutically acceptable and compatible with the active ingredient. For oral administration, the SARM agents or their physiologically tolerated derivatives such as salts, esters, N-oxides, and the like are mixed with additives customary for this purpose, such as vehicles, stabilizers, or inert diluents, and converted by customary methods into suitable forms for administration, such as tablets, coated tablets, hard or soft gelatin capsules, aqueous, alcoholic or oily solutions. For parenteral administration, the SARM agents or their physiologically tolerated derivatives such as salts, esters, N-oxides, and the like are converted into a solution, suspension, or emulsion, if desired with the substances customary and suitable for this purpose, for example, solubilizers or other.

An active component can be formulated into the composition as neutralized pharmaceutically acceptable salt forms. Pharmaceutically acceptable salts include the acid addition salts (formed with the free amino groups of the polypeptide or antibody molecule), which are formed with inorganic acids such as, for example, hydrochloric or phosphoric acids, or such organic acids as acetic, oxalic, tartaric, mandelic, and the like. Salts formed from the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

For use in medicine, the salts of the SARM will be pharmaceutically acceptable salts. Other salts may, however, be useful in the preparation of the compounds according to the invention or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, methanesulphonic acid, fumaric acid, maleic acid, succinic acid, acetic acid, benzoic: acid, oxalic acid, citric acid, tartaric acid, carbonic acid or phosphoric acid.

As defined herein, "contacting" means that the SARM compound of the present invention is introduced into a sample containing the enzyme in a test tube, flask, tissue culture, chip, array, plate, microplate, capillary, or the like, and incubated at a temperature and time sufficient to permit binding of the SARM to the enzyme. Methods for contacting the samples with the SARM or other specific binding components are known to those skilled in the art and may be selected depending on the type of assay protocol to be run. Incubation methods are also standard and are known to those skilled in the art.

In another embodiment, the term "contacting" means that the SARM compound of the present invention is introduced into a subject receiving treatment, and the SARM compound is allowed to come in contact with the androgen receptor in vivo.

As used herein, the term "treating" includes preventative as well as disorder remitative treatment. As used herein, the terms "reducing", "suppressing" and "inhibiting" have their commonly understood meaning of lessening or decreasing. As used herein, the term "progression" means increasing in scope or severity, advancing, growing or becoming worse. As used herein, the term "recurrence" means the return of a disease after a remission.

As used herein, the term "administering" refers to bringing a subject in contact with a SARM compound of the present invention. As used herein, administration can be accomplished in vitro, i.e. in a test tube, or in vivo, i.e. in cells or tissues of living organisms, for example humans. In one embodiment, the present invention encompasses administering the compounds of the present invention to a subject.

In one embodiment, the methods of the present invention comprise administering a SARM compound as the sole active ingredient. However, also encompassed within the scope of the present invention are methods or treating BPH as disclosed herein, which comprise administering the SARM compounds in combination with one or more therapeutic agents. These agents include, but are not limited to: LHRH analogs, reversible antiandrogens, antiestrogens, anticancer drugs, 5-alpha reductase inhibitors, aromatase inhibitors, progestins, or agents acting through other nuclear hormone receptors.

In one embodiment, the present invention provides compositions and pharmaceutical compositions comprising a selective androgen receptor modulator compound, in combination with an LHRH analog. In another embodiment, the present invention provides compositions and pharmaceutical compositions comprising a selective androgen receptor modulator compound, in combination with a reversible antiandrogen. In another embodiment, the present invention provides compositions and pharmaceutical compositions comprising a selective androgen receptor modulator compound, in combination with an antiestrogen. In another embodiment, the present invention provides compositions and pharmaceutical compositions comprising a selective androgen receptor modulator compound, in combination with an anticancer drug. In another embodiment, the present invention provides compositions and pharmaceutical compositions comprising a selective androgen receptor modulator compound, in combination with a 5-alpha reductase inhibitor. In another embodiment, the present invention provides compositions and pharmaceutical compositions comprising a selective androgen receptor modulator compound, in combination with an aromatase inhibitor. In another embodiment, the present invention provides compositions and pharmaceutical compositions comprising a selective androgen receptor modulator compound, in combination with a progestin. In another embodiment, the present invention provides compositions and pharmaceutical compositions comprising a selective androgen receptor modulator compound, in combination with an agent acting through other nuclear hormone receptors.

The following examples are presented in order to more fully illustrate the preferred embodiments of the invention. They should in no way, however, be construed as limiting the broad scope of the invention.

EXPERIMENTAL DETAILS SECTION

Example 1

Interaction Between Compound VI and Human 5α-Reductase

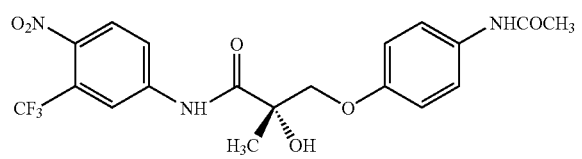

VI

Testosterone can be reduced by the enzyme 5•-reductase to dihydrotestosterone (DHT). DHT binds with five-fold greater affinity to the human androgen receptor and is thought to be the mediator of androgen effects in many tissues. Since Compound VI mimics the effects of testosterone in many in vitro and in vivo systems, Compound VI was tested to determine whether it interacts with 5α-reductase. This study (1) determined if Compound VI is a substrate for 5α-reductase, and (2) determined if Compound VI has any effects on the conversion of testosterone to DHT via 5α-reductase.

Methods: COS1 (American Type Culture Collection, Manassas, Va.) cells were plated in twelve-well plates at a density of 60,000 cells/well and transiently transfected with expression vectors for human 5•-reductase (obtained from Dr. David W. Russell, Southwestern Medical Center, Dallas, Tex.). LipofectAMINE PLUS™ Reagent (Invitrogen, Carlsbad, Calif.) was used for transfection. pCMV•SPORT-•gal plasmid (Invitrogen, Carlsbad, Calif.) was co-transfected to monitor transfection efficiency. Forty-eight hours after transfection, testosterone (4 μM) and/or Compound VI (2 or 200 μM) were added to the medium and incubated at 37° C. Aliquots of the culture medium were removed after 2 hours and the reaction stopped by addition of ice-cold acetonitrile (1:1, vol:vol). Testosterone and Compound VI concentrations in the incubate were determined by HPLC using a reversed-phase column (μBondaPak C18, 3.9×300 mm, Waters Corporation, Milford, Mass.) and a mobile phase of 38% acetonitrile in deionized water at a flow rate of 1.5 ml/min. Analytes were detected by UV absorbance at 254 nm. Calibration curves were prepared using the peak areas to calculate the concentration of testosterone or Compound VI in the incubate at the completion of the reaction. Cells were lysed after the reaction and the cellular supernatant used to determine •-galactosidase activity and ensure equal transfection efficiency between wells.

Results: Incubation of Compound VI (2 μM) with 5α-reductase type 1 or type 2 showed that it is not metabolized by this enzyme (FIG. 1). The concentration of Compound VI was unchanged over the 2-hour incubation period, indicating that Compound VI is not a substrate for these enzymes. Testosterone (4 μM) was rapidly converted to DHT when incubated with 5α-reductase type 1 or type 2, decreasing by 34% and 35%, respectively, in the presence of these enzymes. The conversion of testosterone to DHT was inhibited by the presence of Compound VI, with less than 10% decreases in testosterone concentration being observed in the presence of Compound VI (2•M or 200 •M). These data demonstrate that Compound VI is a competitive inhibitor of 5α-reductase type 1 and type 2, thus having inhibitory effects of Compound VI on prostate and seminal vesicle weight previously observed by Applicants in intact and hemi-orchidectomized animals.

Compound VI is not a substrate but acts as a competitive inhibitor of 5α-reductase type 1 and type 2.

Example 2

Pharmacologic Activity and Tissue Selectivity of Compound VI in Rats of Varying Hormonal Status Selective androgen receptor modulators (SARMs) have a wide variety of potential therapeutic applications, including male hypogonadism, osteoporosis, muscle-wasting diseases, sexual libido and contraception. Previous studies by Applicants demonstrated that Compound VI is a potent and efficacious selective androgen receptor modulator (SARM) in castrated male rats. Applicants completed a preclinical study to compare the pharmacologic effects and tissue-selectivity of Compound VI and testosterone propionate (TP) in male rats of varying hormonal status. Male rats with normal testicular function (i.e., intact with no surgical manipulation) were included to examine the effects of Compound VI on animals with normal blood levels of testosterone. Male rats that received unilateral orchidectomy (i.e., surgical removal of one testis) were included to examine the effects of Compound VI on animals with slight androgen depletion. Male rats that received bilateral orchidectomy (i.e., surgical removal of both testes) were included to examine the effects of Compound VI on androgen-deficient animals.

Methods: Compound VI was synthesized and characterized in the laboratory of Dr. Duane Miller at the University of Tennessee, Memphis, Tenn. Male Sprague-Dawley rats were purchased from Harlan Biosciences (Indianapolis, Ind.). The animals were maintained on a 12-h cycle of light and dark with food and water available ad libitum. All animal studies were reviewed and approved by the Animal Care and Use Committee of The Ohio State University, and conformed to the Principles of Laboratory Animal Care. Immature male Sprague-Dawley rats weighing 187 to 214 were randomly distributed into 9 groups of 5 animals. One day before the initiation of drug treatment, groups 4 through 6 and groups 7 through 9 received unilateral or bilateral orchidectomy, respectively, via a midline scrotal incision. Groups 1 through 3 did not undergo surgery. All drugs given to animals were freshly prepared as solutions in polyethylene glycol 300 (PEG 300). Groups 4 and 7 received treatment with vehicle alone (i.e., PEG 300). Animals in groups 3, 6, and 9 received testosterone propionate (TP, 0.5 mg/day) via implantation of subdermal osmotic pumps (Model 2002, Durect Corporation, Palo Alto, Calif.). Animals in groups 2, 5, and 8 received Compound VI (0.5 mg/day) via implantation of subdermal osmotic pumps. After 14 days of drug treatment, rats were weighed, anesthetized, and sacrificed. Blood samples were collected by venipuncture of the abdominal aorta. Plasma samples were analyzed for testosterone, FSH, LH and osteocalcin. Testosterone concentrations were measured by AniLytics Inc. (Gaithersburg, Md.). FSH and LH levels were measured by the National Hormone and Peptide Program (Dr. A F Parlow, UCLA, CA). Plasma osteocalcin levels were determined using a commercially available rat osteocalcin EIA kit from Biomedical Technologies Inc. (Stoughton, Mass.). The ventral prostates, seminal vesicles, and levator ani muscle were removed and weighed. Osmotic pumps were also removed from animals to check for correct pump operation. The weights of all organs were normalized to body weight, and analyzed for any statistically significant differences between groups using single-factor ANOVA with the alpha value set a priori at p<0.05. The weights of prostates and seminal vesicles were used as indices for evaluation of androgenic activity, and the levator ani muscle weight was used to evaluate the anabolic activity. Statistical analyses of parameters from complete blood count or serum chemical profiling, wherever applicable, were performed by single-factor ANOVA with the alpha value set a priori at p<0.05.

Results: Plasma testosterone levels were significantly lower in castrated rats, regardless of the treatment group (Table 1 below). Unilateral orchidectomy led to a slight but statistically insignificant decrease in plasma testosterone concentrations. Castrated male rats that received exogenous TP (0.5 mg/day) had higher plasma testosterone levels than vehicle-treated and Compound VI treated controls. However, there were no significant differences in plasma testosterone levels between hemi-orchidectomized animals in any of the treatment groups. Compound VI treatment did not affect testosterone levels in intact, hemi-orchidectomized or castrated male rats, demonstrating that Compound VI has little to no effect on endogenous androgen production at pharmacologically relevant doses.

TABLE 1

Plasma testosterone levels (ng/ml) in different treatment groups (n = 5).

| | Control | Compound VI (0.5 mg/day) | TP (0.5 mg/day) |
|---|---|---|---|
| Intact | 2.674 ± 1.476 | 1.830 ± 0.510 | 1.482 ± 0.416 |
| Hemi-orchidectomized | 1.740 ± 1.049 | 1.404 ± 0.810 | 2.366 ± 1.232 |
| Castrated | 0.036 ± 0.075 † ‡ | 0.066 ± 0.148 † ‡ | 0.258 ± 0.103 * † ‡ |

* $p < 0.05$ compared to control group.
† $p < 0.05$ compared to intact group.
‡ $p < 0.05$ compared to hemi-orchidectomized group.

Plasma FSH and LH levels (Table 2 and 3 on next page) significantly increased in animals that received bilateral orchidectomy (i.e., castrated controls). Plasma FSH levels and LH levels in hemi-orchidectomized animals were not significantly different than intact animals, corroborating the observation that unilateral orchidectomy had no effect on plasma testosterone levels or the pituitary hormones that regulate it. Treatment with TP caused a significant decrease in FSH and LH levels in castrated male rats, indicating that TP suppresses pituitary hormone production. However, Compound VI had no effect on plasma FSH and LH levels. These data indicate that Compound VI has no effect on pituitary hormone production and is therefore advantageous to TP for use in intact animals. No significant differences in FSH or LH levels were observed in intact or hemi-orchidectomized animals.

TABLE 2

Plasma FSH levels (ng/ml) in different treatment groups (n = 5).

| | Control | Compound VI (0.5 mg/day) | TP (0.5 mg/day) |
|---|---|---|---|
| Intact | 13.0 ± 1.3 | 14.4 ± 1.7 | 11.4 ± 1.7 |
| Hemi-orchidectomized | 18.0 ± 1.9 † | 15.2 ± 2.2 | 17.2 ± 3.3 † |
| Castrated | 68.6 ± 6.3 † ‡ | 69.6 ± 11.7 † ‡ | 58.0 ± 6.9 * † ‡ |

* $p < 0.05$ compared to control group.
† $p < 0.05$ compared to intact group.
‡ $p < 0.05$ compared to hemi-orchidectomized group.

TABLE 3

Plasma LH levels (ng/ml) in different treatment groups (n = 5).

| | Control | Compound VI (0.5 mg/day) | TP (0.5 mg/day) |
|---|---|---|---|
| Intact | 0.160 ± 0.187 | 0.026 ± 0.037 | 0.168 ± 0.173 |
| Hemi-orchidectomized | 0.240 ± 0.268 | 0.124 ± 0.115 | 0.124 ± 0.092 |
| Castrated | 8.704 ± 1.709 † ‡ | 8.644 ± 2.799 † ‡ | 6.702 ± 1.513 † ‡ |

* $p < 0.05$ compared to control group.
† $p < 0.05$ compared to intact group.
‡ $p < 0.05$ compared to hemi-orchidectomized group.

The effects of unilateral orchidectomy, bilateral orchidectomy, TP, and Compound VI on plasma osteocalcin levels (Table 4) were examined. Osteocalcin is a specific osteoblastic marker that can be used to evaluate the endogenous bone formation rate. There were no significant differences in osteocalcin levels between intact, hemi-orchidectomized and castrated animals in the vehicle-treated (i.e., control) animals. However, treatment with Compound VI led to a significant increase in plasma osteocalcin levels in hemi-orchidectomized and castrated animals. TP had no effect on plasma osteocalcin levels. These data demonstrate that Compound VI increases bone formation rate in male animals with no effects on plasma concentrations of testosterone, FSH, or LH.

TABLE 4

Plasma osteocalcin levels (ng/ml) in different treatment groups (n = 5).

| | Control | Compound VI (0.5 mg/day) | TP (0.5 mg/day) |
|---|---|---|---|
| Intact | 59.403 ± 13.933 | 55.584 ± 9.715 | 74.952 ± 15.399 |
| Hemi-orchidectomized | 62.110 ± 14.770 | 89.804 ± 15.517*† | 77.236 ± 24.418 |
| Castrated | 66.965 ± 11.305 | 94.215 ± 12.568*† | 65.976 ± 11.213 |

*$p < 0.05$ compared to control group.
†$p < 0.05$ compared to intact group.
‡$p < 0.05$ compared to hemi-orchidectomized group.

In intact animals, Compound VI decreased the size of the prostate to 79% of that observed in control animals, with no statistically significant changes in the size of the seminal vesicles or levator ani muscle (Table 5 below and FIG. 2). The pharmacologic effects and tissue selectivity of Compound VI were more obvious in hemi-orchidectomized animals. Compound VI decreased the size of the prostate and seminal vesicles to 75% and 79%, respectively, and increased the size of the levator ani muscle to 108% of that observed in untreated hemi-orchidectomized animals. These observations demonstrate that Compound VI acts as a partial agonist in prostate and seminal vesicles and as a full agonist in levator ani muscle. No adverse pharmacologic effects were observed.

TABLE 5

Comparison of androgenic and anabolic effects of Compound VI and TP on intact, hemi-orchidectomized and castrated rats (% of intact control, n = 5).

| Organs | | Control | COMPOUND VI (0.5 mg/day) | TP (0.5 mg/day) |
|---|---|---|---|---|
| Prostate | Intact | 100.00 ± 13.13 | 79.41 ± 9.32*† | 97.45 ± 10.82 |
| | Hemi- | 86.42 ± 19.52 | 74.69 ± 8.44*† | 98.57 ± 7.98 |
| | Castrated | 7.19 ± 1.25 | 32.55 ± 11.65*†‡ | 76.78 ± 10.43*‡ |
| Seminal | Intact | 100.00 ± 18.84 | 90.54 ± 12.10 | 103.95 ± 13.23 |
| Vesicle | Hemi- | 102.93 ± 7.47 | 78.55 ± 13.58†‡ | 114.19 ± 23.81 |
| | Castrated | 8.97 ± 1.23 | 16.47 ± 5.21*†‡ | 63.48 ± 17.05*‡ |
| Levator | Intact | 100.00 ± 12.69 | 109.15 ± 14.68 | 95.61 ± 9.34 |
| Ani | Hemi- | 92.94 ± 7.83 | 108.10 ± 8.92‡ | 98.63 ± 10.47 |
| | Castrated | 42.74 ± 5.22 | 100.65 ± 10.86‡ | 87.27 ± 10.25‡ |

*$p < 0.05$ compared to intact control group.
†$p < 0.05$ compared to TP of same surgical status (i.e., intact, hemi-orchidectomized, or castrate).
‡$p < 0.05$ compared to control group of same surgical status.

Compound VI demonstrated potent and tissue-selective pharmacologic effects in intact, hemi-orchidectomized and castrated male rats. Compound VI led to significant decreases in prostate weights in intact and hemi-orchidectomized animals, and was less effective than TP at increasing the weight of the prostate in castrated animals. Similar pharmacologic effects were noted in the seminal vesicles (another organ generally considered as a marker of androgenic effects), with the exception that Compound VI had no effect on the weight of the seminal vesicles in intact animals. Compound VI treatment led to significant increases in the weight of the levator ani muscle in hemi-orchidectomized and castrated animals. These effects were greater than those observed with TP. These data demonstrate the tissue-selective pharmacologic effects of Compound VI. It is important to note that these effects were observed in the absence of any significant changes in plasma concentrations of FSH, LH and testosterone. Compound VI increased plasma concentrations of osteocalcin. In summary, these data show that Compound VI elicits an optimal pharmacological profile in male animals, identifying it as the first member of a new class of orally bioavailable and tissue-selective SARMs.

Example 3

Pharmacologic Activity and Tissue-Selectivity of Compound VII, Hydroxy-flutamide and Finasteride in Intact Male Rats Compound VII is a selective androgen receptor modulator (SARM) in castrated male rats. It behaved as an agonist in anabolic tissue while a partial agonist in androgenic tissue. When it's administered to intact male rats at the dose rate of 0.5 mg/day, Compound VII significantly decreased the prostate weight to 63% of that observed in vehicle-treated intact animals without affecting the levator ani muscle weight. The tissue selectivity Compound VII demonstrated in intact male rats could be explained by two possible mechanisms; 1) in the presence of endogenous testosterone, Compound VII simply behaved as a partial agonist in DHT-dependent androgenic tissue; 2) Compound VII is also a 5α-reductase inhibitor besides its partial agonist activity in androgenic tissues.

Methods: Male Sprague-Dawley rats were purchased from Harlan Biosciences (Indianapolis, Ind.). The animals were maintained on a 12-h cycle of light and dark with food and water available ad libitum. Male Sprague-Dawley rats weighing 189 to 226 g were randomly distributed into groups of 5 animals. The intact male rats were treated with hydroxyflutamide (0.5, 1, 5, 10 or 25 mg/kg), finasteride (5 mg/kg), Compound VII (0.5, 1, 5, 10, 25 mg/kg) or vehicle for 3, 6, or 9 days. The drugs were dissolved in DMSO:PEG300 (20:80, v:v) and administered via daily subcutaneous injections, and the dosages were adjusted based on animal's body weight, which was measured on a daily basis. A group of castrated rats (n=5) was also included as control for each time point. By the end of each treatment period, the animals were sacrificed within 8 hours after the last dose, the androgenic and anabolic tissues (ventral prostate, seminal vesicle and levator ani muscle) were removed and weighed, the prostate was frozen and stored at −80° C. for analyzing tissue concentrations of DHT and testosterone, and blood samples were collected and used for the measurement of serum markers, including FSH, LH and testosterone. The organ weights were normalized with the body weights. Percentage changes were determined by comparison to intact animals. Statistical analyses of all the parameters were performed by single-factor ANOVA with the alpha value set a priori at $p<0.05$.

Figure 3:
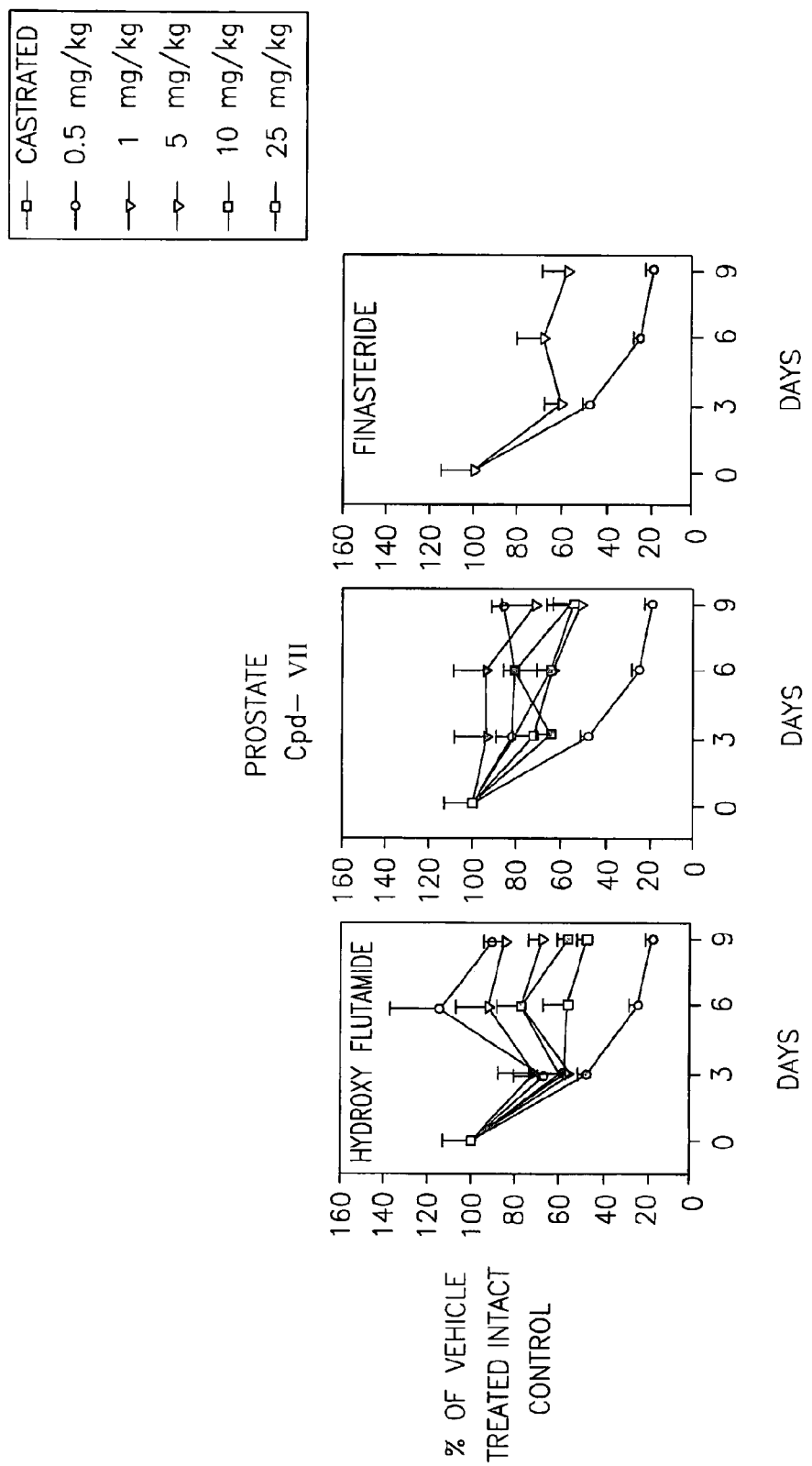
FIG. 3. Pharmacological effects of hydroxy-flutamide, Compound VII and finasteride on the ventral prostate weights in intact male rats after different treatment periods (n=5).
Figure 4:
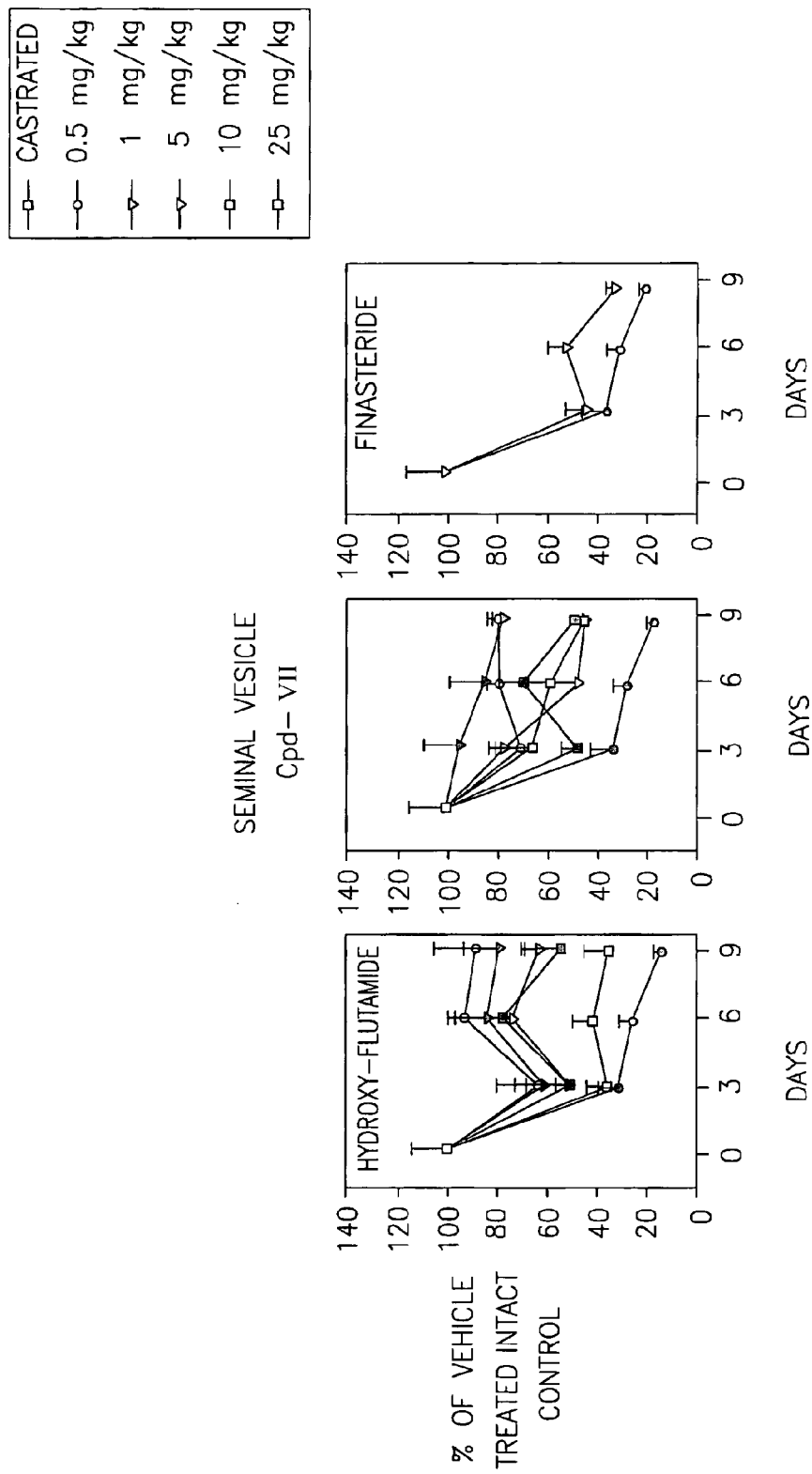
FIG. 4. Pharmacological effects of hydroxy-flutamide, Compound VII and finasteride on the seminal vesicle weights in intact male rats after different treatment periods (n=5).
Figure 5:
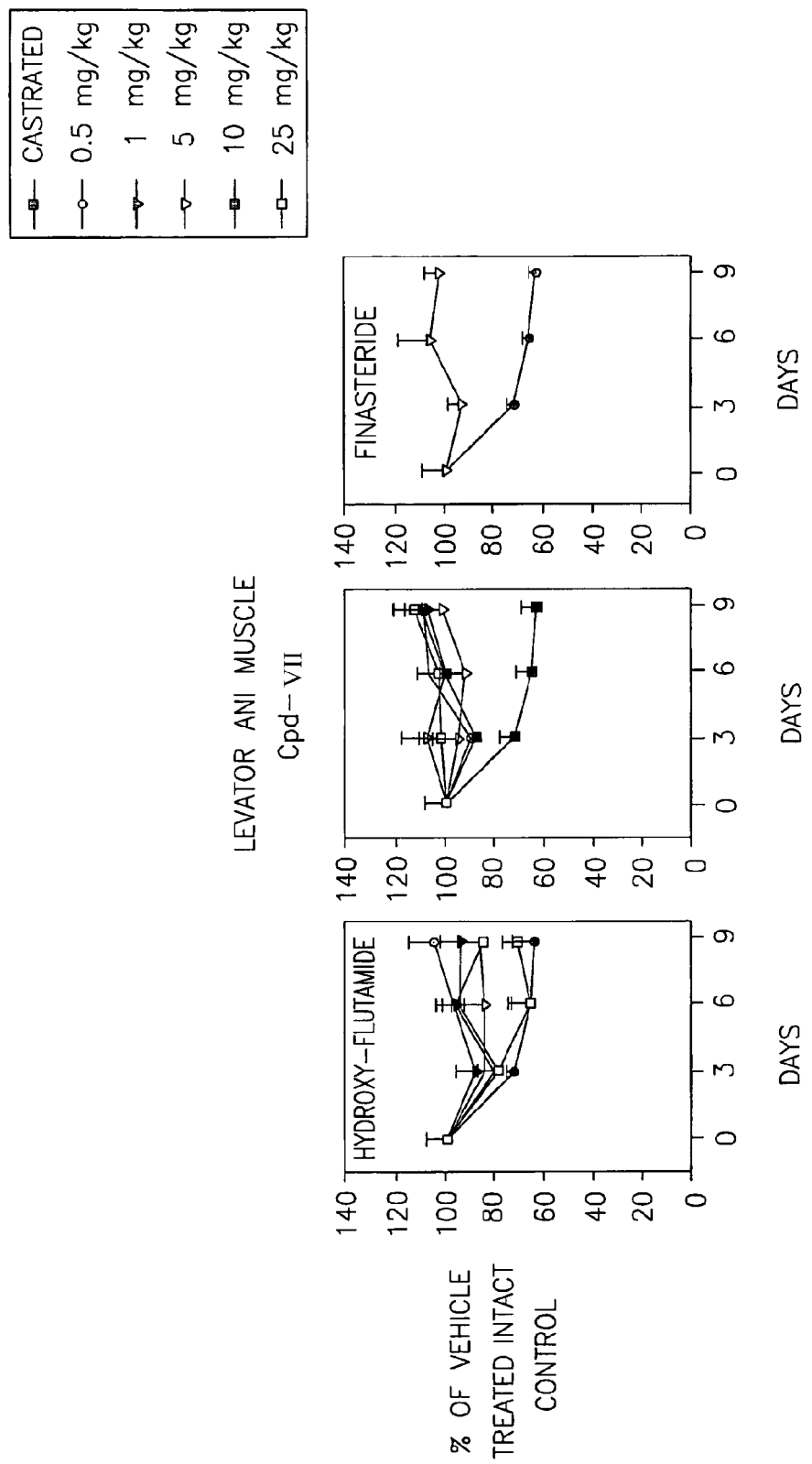
FIG. 5. Pharmacological effects of hydroxy-flutamide, Compound VII and finasteride on the levator ani muscle weights in intact male rats after different treatment periods (n=5).

Results: FIGS. 3 to 5 show the change in organ weights in all treatment groups after different treatment periods. Hydroxyflutamide at all doses (0.5, 1, 5, 10, mg/kg), significantly decreased the wet weight of the prostate, seminal vesicle and levator ani muscle within three days of treatment. However, no typical dose-response relationship was observed in any of these organs. Similar in all the dose groups, the prostate, seminal vesicle and levator ani muscle were significantly decreased to approximately 60%, 50% and 85%, respectively. There was no significant difference between any two of these dose groups. At the same time point, castration significantly decreased the prostate, seminal vesicle and levator ani muscle to 45%, 30% and 71%, respectively. In Compound VII treated groups, no typical dose-response relationship was observed either, similar results were observed in most of the dose groups (0.5, 1, 5, 10, 25 mg/kg) after three days of treatment. In general, Compound VII decreased the prostate and seminal vesicle weights to 80% and 70%, without affecting the levator ani muscle weight. At the same stage, finasteride (5 mg/kg) significantly decreased the prostate and seminal vesicle weight to 59% and 38%, while showing no effect on the levator ani muscle weight.

Six days after castration, the prostate, seminal vesicle and levator ani muscle weights decreased further to 22%, 24% and 65% of the normal levels. However, the organ weight changes in hydroxy-flutamide treated animals did not follow the pattern observed after three days treatment. In the lower dose groups (0.5, 1, 5, 10 mg/kg) of hydroxy-flutamide treated animals, no further decreases were observed in any of the organ weights. On the contrary, the organ weights in these dose groups returned to the levels observed in intact animals. Only the highest dose (25 mg/kg) significantly decreased the prostate, seminal vesicle and levator ani muscle to 54%, 41% and 65%, respectively. Although no apparent dose-response relationship was observed in these hydroxy-flutamide treated groups, the highest dose group started to show significant difference from all the lower dose groups. In Compound VII treated animals, changes in prostate, seminal vesicle, and levator ani muscle were similar to that observed after three days treatment, no typical dose-response relationship was observed. At higher doses (5, 10, 25 mg/kg), significant decreases in the prostate and seminal vesicle weights were observed, ranging from 70 to 80% for the prostate, and 45 to 68% for the seminal vesicle. Importantly, none of these doses caused any significant changes in the levator ani muscle weights, demonstrating the tissue-selective pharmacologic activity of Compound VII and its potential value in the treatment of BPH. Finasteride (5 mg/kg) significantly decreased the prostate, seminal vesicle weights to 67% and 47%, and no significant changes were seen in levator ani muscle weight.

Nine days after castration, the prostate, seminal vesicle and levator ani muscle weights decreased even further to 15%, 14% and 62%, respectively. Organ weight changes observed in finasteride (5 mg/kg) treated animals were similar to those observed after three or six days of treatment. The prostate and seminal vesicle weights were decreased to 55% and 29%, the levator ani muscle weight was not significantly changed. In Compound VII treated groups, increasing effects in decreasing the prostate and seminal vesicle weights were shown in lower dose groups (0.5, 1, 5 mg/kg). However, decreases in all the high doses (5, 10, 25 mg/kg) were not dose-dependent, the prostate and seminal vesicle weights were significantly decreased to 50% and 45%, respectively. Also, no significant changes in the levator ani muscle weights were observed in most of the dose groups after nine days treatment, except for that significant increase (112%) was seen in the highest dose group (25 mg/kg). The hydroxy-flutamide treatment finally showed some dose-response relationship after nine days treatment. Different from what was observed after six days treatment, moderate decreases were seen in the prostate, seminal vesicle and levator ani muscle weights at lower doses (0.5, 1, 5, 10 mg/kg), and the changes were dose-dependent. The 25 mg/kg dose maintained its effects on all the organ weights at a similar level compared to that at previous time points.

In summary, high dose (25 mg/kg) of hydroxy-flutamide significantly decreased the organ weights of the prostate, seminal vesicle and levator ani muscle after 3, 6 or 9 days treatment. However, some fluctuations in the changes were seen in the lower dose groups (0.5, 1, 5, 10 mg/kg), and no typical dose-response relationship was observed until the end of the nine days treatment. Finasteride, at 5 mg/kg dose, significantly decreased the prostate and seminal vesicle weights to similar extend after 3, 6 or 9 days treatment, while it did not affect the levator ani muscle weight. Compound VII was also able to decrease the prostate and seminal vesicle weights in intact animals after 3, 6 or 9 days treatment, and no typical dose-response relationship was observed at 3 and 6 day time point, although some dose-dependent changes were seen at lower doses (0.5, 1, 5 mg/kg) after 9 days treatment. However, Compound VII did not significantly decrease the levator ani muscle weights at any of the doses after 3, 6 or 9 days treatment, 25 mg/kg dose treatment even increased the levator ani muscle weight by 12% after 9 days treatment. The effects of Compound VII on the androgenic tissues were similar to those of hydroxy-flutamide, while its effect on the levator ani muscle was similar to that of finasteride.

Example 4

Figure 6:
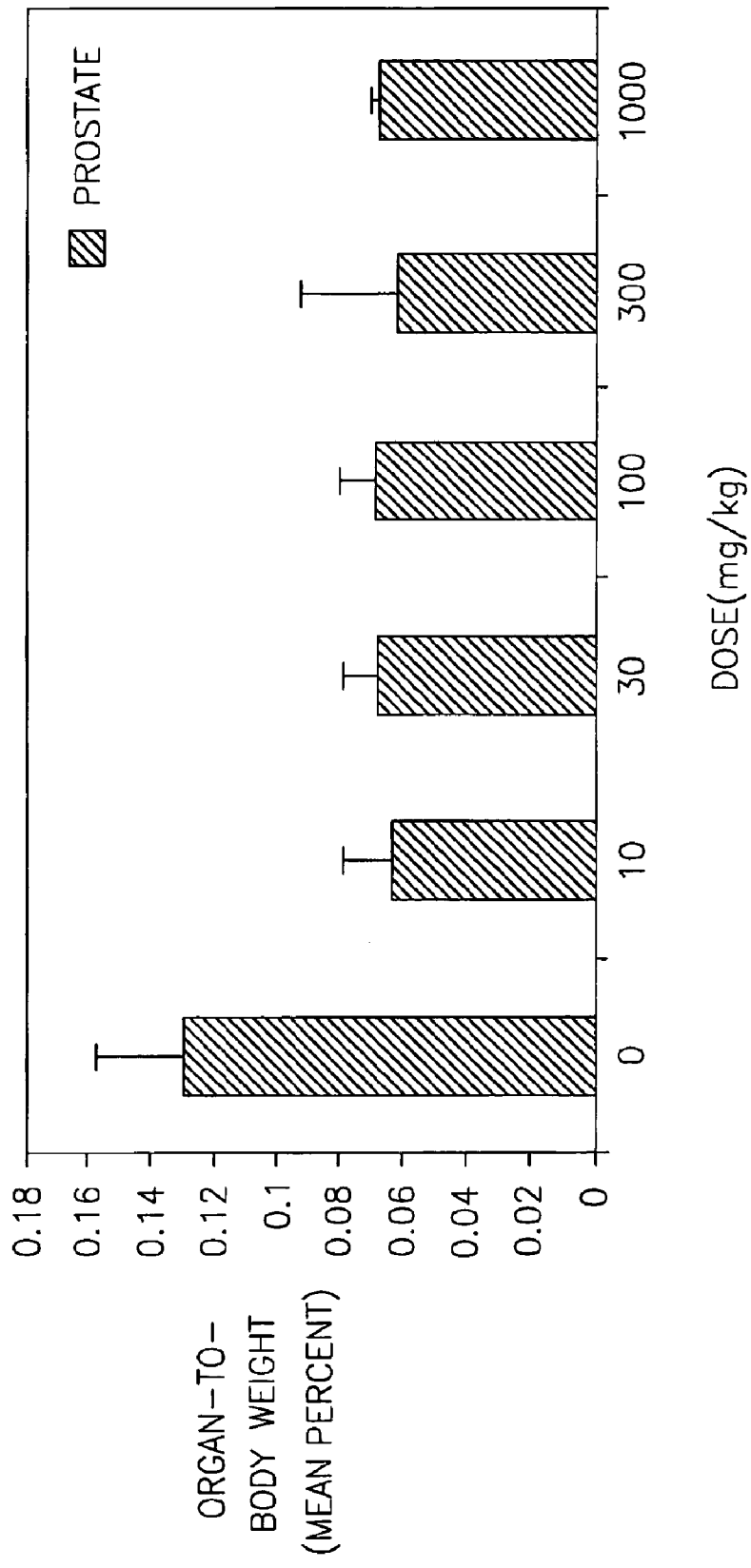
FIG. 6. Compound VII reduces prostate in intact Sprague-Dawley rats.

Compound VII Reduces Prostate in Intact Sprague-Dawley Rats 20 intact male Sprague-Dawley rats, weighing approximately 100-175 grams each, were randomly placed into 4 treatment groups of 5 animals/group. Animals were treated by oral gavage with vehicle (10% Ethanol and 90% Polyethylene Glycol) or Compound VII (dissolved in the vehicle) according to following treatment groups: Group 1=0 mg/kg (vehicle only), Group 2=Compound VII, 30 mg/kg; Group 3=Compound VII, 100 mg/kg; Group 4=Compound VII, 300 mg/kg. Each animal received once-daily doses for seven consecutive days. On day 8, the animals were sacrificed and the ventral prostate from each animal was dissected and weighed. Prostate weights (g) were normalized to body weight (g), and the results are shown in FIG. 6. Animals treated with 10 mg/kg of Compound VII demonstrated a markedly decreased prostate-to-Body weight ratio of 0.62% relative to 0.128% in the 0 mg/kg control group (Group 1). In all treatment groups, Compound VII dramatically reduced the prostate weight (normalized to body weight) by greater than 48.4% when compared to the intact control (p<0.01). Further, increasing the dose 100-fold above 10 mg/kg day did not significantly increase the atrophy in prostate (10 mg/kg compared to 1000 mg/kg). The results demonstrate herein show that Compound VII will be an effective intervention for reducing the size of the prostate and therefore minimizing the symptoms associated with benign prostate hyperplasia at relatively low pharmacological doses.

It will be appreciated by a person skilled in the art that the present invention is not limited by what has been particularly shown and described hereinabove. Rather, the scope of the invention is defined by the claims which follow:

What is claimed is:
1. A method of reducing the severity or frequency of signs and symptoms of benign prostate hyperplasia (BPH) in a subject suffering from BPH, comprising a step of contacting the androgen receptor with a selective androgen receptor modulator (SARM) compound represented by the structure of formula I:

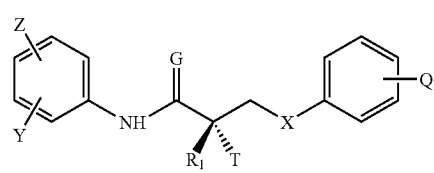

I wherein
G is O;
X is O;
T is OH, OR, —NHCOCH$_3$, or NHCOR;
Z is NO$_2$, CN, COOH, COR, NHCOR or CONHR;
Y is CF$_3$, F, I, Br, Cl, CN, C(R)$_3$ or Sn(R)$_3$;
Q is alkyl, halogen, CF$_3$, CN, C(R)$_3$, Sn(R)$_3$, N(R)$_2$, NHCOCH$_3$, NHCOCF$_3$, NHCOR, NHCONHR, NHCOOR, OCONHR, CONHR, NHCSCH$_3$, NHCSCF$_3$, NHCSR, NHSO$_2$CH$_3$, NHSO$_2$R, OR, COR, OCOR, OSO$_2$R, SO$_2$R, or SR;
R is alkyl, haloalkyl, dihaloalkyl, trihaloalkyl, CH$_2$F, CHF$_2$, CF$_3$, CF$_2$CF$_3$, aryl, phenyl, halogen, alkenyl or OH; and
R$_1$ is CH$_3$, CH$_2$F, CHF$_2$, CF$_3$, CH$_2$CH$_3$, or CF$_2$CF$_3$.

2. The method of claim 1, wherein said SARM compound is represented by the structure of formula II:

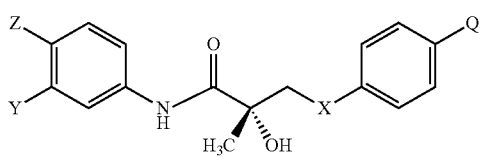

wherein Z, Y, X and Q are as described in claim 1.

3. The method according to claim 2, wherein said SARM compound is:

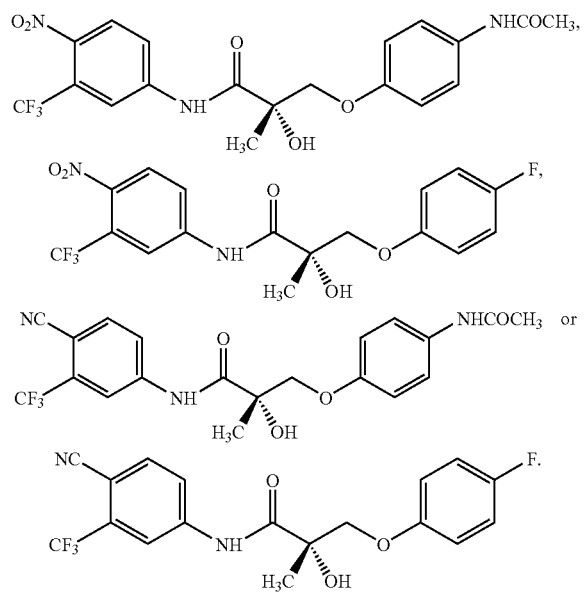

4. The method of claim 1, wherein said subject is a human.
5. The method of claim 1, wherein said SARM is an inhibitor of a 5α-reductase enzyme.
6. The method of claim 1, wherein said SARM is a competitive inhibitor of a 5-α reductase enzyme.
7. The method of claim 5, wherein said 5-α reductase enzyme is a 5-α reductase enzyme type 1.
8. The method of claim 5, wherein said 5-α reductase enzyme is a 5-α reductase enzyme type 2.
9. The method of claim 5, wherein said 5-α reductase enzyme is a testosterone 5-α reductase enzyme.
10. A method of treating a subject suffering from hair loss, comprising a step of administering to said subject a therapeutically effective amount of a 5-α reductase enzyme inhibitor, wherein said inhibitor is a selective androgen receptor modulator (SARM) compound represented by the structure of formula I:

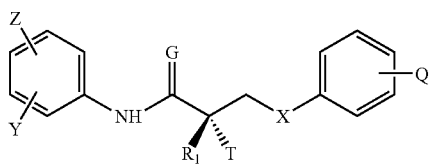

wherein
G is O;
X is O;
T is OH, OR, —NHCOCH$_3$, or NHCOR;
Z is NO$_2$, CN, COOH, COR, NHCOR or CONHR;
Y is CF$_3$, F, I, Br, Cl, CN, C(R)$_3$ or Sn(R)$_3$;
Q is alkyl, halogen, CF$_3$, CN, C(R)$_3$, Sn(R)$_3$, N(R)$_2$, NHCOCH$_3$, NHCOCF$_3$, NHCOR, NHCONHR, NHCOOR, OCONHR, CONHR, NHCSCH$_3$, NHCSCF$_3$, NHCSR, NHSO$_2$CH$_3$, NHSO$_2$R, OR, COR, OCOR, OSO$_2$R, SO$_2$R, or SR;
R is alkyl, haloalkyl, dihaloalkyl, trihaloalkyl, CH$_2$F, CHF$_2$, CF$_3$, CF$_2$CF$_3$, aryl, phenyl, halogen, alkenyl or OH; and
R$_1$ is CH$_3$, CH$_2$F, CHF$_2$, CF$_3$, CH$_2$CH$_3$, or CF$_2$CF$_3$.

11. The method of claim 10, wherein said SARM compound is represented by the structure of formula II:

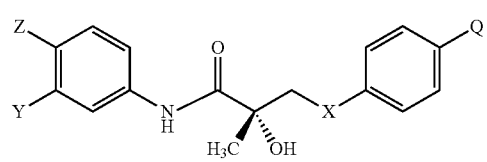

wherein Z, Y, X and Q are as described in claim 10.

12. The method according to claim 10, wherein said SARM compound is:

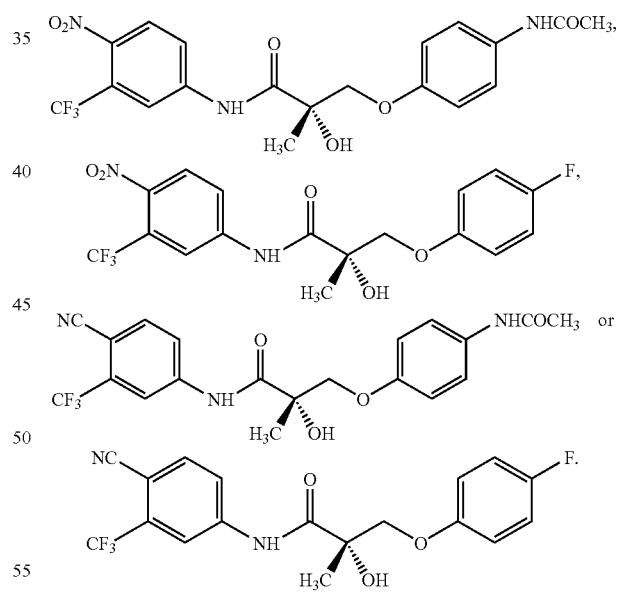

13. The method of claim 10, wherein said subject is a human.
14. The method of claim 1, wherein said SARM compound is a pharmaceutically acceptable salt.
15. The method of claim 10, wherein said SARM compound is a pharmaceutically acceptable salt.

* * * * *